(12) United States Patent
Kutay et al.

(10) Patent No.: US 9,884,964 B2
(45) Date of Patent: Feb. 6, 2018

(54) ASPHALT FOAM COLLAPSE TEST METHODS AND RELATED APPARATUS

(71) Applicant: BOARD OF TRUSTEES OF MICHIGAN STATE UNIVERSITY, East Lansing, MI (US)

(72) Inventors: Muhammed Emin Kutay, Okemos, MI (US); Hande Isik Ozturk, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 700 days.

(21) Appl. No.: 14/299,483

(22) Filed: Jun. 9, 2014

(65) Prior Publication Data

US 2014/0360406 A1 Dec. 11, 2014

Related U.S. Application Data

(60) Provisional application No. 61/833,232, filed on Jun. 10, 2013.

(51) Int. Cl.
*C08L 95/00* (2006.01)
*G01N 33/42* (2006.01)

(52) U.S. Cl.
CPC ............ *C08L 95/00* (2013.01); *G01N 33/42* (2013.01); *C08L 2555/10* (2013.01)

(58) Field of Classification Search
CPC .... C08L 95/00; C08L 95/005; C08L 2555/00; C08L 2555/10; G01N 33/42; C10C 3/00; G01F 1/00; G01L 31/00; G05B 5/00
See application file for complete search history.

(56) References Cited

U.S. PATENT DOCUMENTS

| 4,692,350 A | * | 9/1987 | Clarke | E01C 19/176 106/122 |
| 2012/0243940 A1 | * | 9/2012 | Thenhaus | A01G 25/165 405/37 |

OTHER PUBLICATIONS

Lee, Hosin David and Kim, Yongjoo "Manual of Laboratory Mix Design Procedure for Cold In-Place Recycling using Foamed Asphalt (CIR-foam)". http://publications.iowa.gov/id/eprint/20040 Accession No. 01586723 Report/Paper No. TR-474. 14 pages Jun. 2007.*

(Continued)

*Primary Examiner* — Jennifer A Smith
*Assistant Examiner* — Alexandra M Moore
(74) *Attorney, Agent, or Firm* — Marshall, Gerstein & Borun LLP

(57) ABSTRACT

The disclosure relates to asphalt foam collapse test methods and related apparatus for the measurement and determination of foamed asphalt binder quality, in particular warm-mix asphalt. Various asphalt binder/foam quality indicators can be measured according to the disclosure, such as bubble size distribution, bubble surface area, foam expansion ratio, foam half-life, foam index, as well as normalized parameters related to the same. The disclosed methods and apparatus permit the repeatable characterization and formation of foamed asphalt compositions, enabling the skilled artisan to form foamed asphalt/aggregate compositions of known, repeatable quality. This enhances the ability to form WMA foamed asphalt concrete with controlled and favorable properties selected for the particular environmental conditions (e.g., climate-, weather-, and/or traffic-related) where the concrete is to be used.

14 Claims, 12 Drawing Sheets

(56) References Cited

OTHER PUBLICATIONS

ASTM Designation D1173-07, "Standard Test Method for Foaming Properties of Surface-Active Agents (a.k.a. Ross and Miles Test)", American Society for Testing and Materials: Philadelphia, PA (2007).
ASTM Designation D1881-97, (Reapproved 2009), "Standard Test Method for Foaming Tendencies of Engine Coolants in Glassware", American Society for Testing and Materials: Philadelphia, PA (1997).
ASTM Designation D3519-88, (Reapproved 2007), "Standard Test Method for Foam in Aqueous Media (Blender Test)", American Society for Testing and Materials: Philadelphia, PA (1988).
ASTM Designation D3601-88, (Reapproved 2007), "Standard Test Method for Foam in Aqueous Media (Bottle Test)", American Society for Testing and Materials: Philadelphia, PA (1988).
ASTM Designation D892-13, "Standard Test Method for Foaming Characteristics of Lubricating Oils", American Society for Testing and Materials: Philadelphia, PA (2013).
Bennert, T. "Evaluation of Warm Asphalt Technology—Feasibility Study" NJDOT Research Project, Center for Advanced Infrastructure and Transportation, Rutgers University, Final Report (2012).
Brennen, M, Tia, M., Altschaeffl, A. and Wood, L.E., "Laboratory Investigation of the Use of Foamed Asphalt for Recycled Bituminous Pavements", Transportation Research Record: Journal of the Transportation Research Board, 911, 80-87 (1983).
Bonaquist, R."Mix Design Practices for Warm Mix Asphalt", NCHRP Report 691, Transportation Research Board of the National Academies. Washington, DC (2011).
D'Angelo, J., Harm, E., Bartozsek, J., Baumgardner, G., Corrigan, M., Cowsert, J., Harman, T., Jamshidi, M., Jones, W., Newcomb, D., Prowell, B., Sines, R. and Yeaton B., " Warm Mix Asphalt: European Practice", FHWA report No. FHWA-PL-08-007 (2008).
Haffmans, B.V., NI BEM Foam Stability Tester product brochure (2004).
Hassan, M. M. "Life-Cycle Assessment of Warm-Mix Asphalt: an Environmental and Economic Perspective" , Transportation Research Board (TRB), 88th Annual Meeting Compendium of Papers DVD, Washington, D.C. (2009).
He, G. and Wong W., "Decay Properties of the Foamed Bitumens", Construction and Building Materials, 20: 866-877 (2006).
Jenkins, K.J., "Mix Design Considerations for Cold and Half-Warm Bituminous Mixes with Emphasis on Foamed Bitumen", Ph.D. Dissertation, University of Stellenbosch, South Africa (2000).
Kim, Y., Lee H., and Heitzman, M. "Validation of New Mix Design Procedure for Cold In-place Recycling with Foamed Asphalt", J. Mater. Civ. Eng., 11 pages (2007).
Kutay, M.E. and Ozturk, H. "Investigation of Moisture Dissipation in Foam-based Warm Mix Asphalt Using Synchrotron-Based X-Ray Microtomography", ASCE M. Mater. Civ. Eng., 24, (6), 674-83 (2012).
Kutay, M.E., Arambula, E., Gibson, N. and Youtcheff, J. "Three-Dimensional Image Processing Methods to Identify and Characterize Aggregates in Compacted Aspháalt Mixtures", International Journal of Pavement Engineering, vol. 11, Issue 6, pp. 511-528 (2010).
Kutay, M.E., Ozturk, H.I., Abbas, A.R. and Hu, C "Comparison of 2D and 3D Image-Based Aggregate Morphological Indices", International Journal of Pavement Engineering, vol. 12, Issue 4, pp. 421-431 (2011).
KristjansdOttir, 0., Muench, S.T., Michael, L. and Burke, G., "Assessing the potential for Warm Mix Technology Adoption", Transportation Research Record: Journal of the Transportation Research Board, No. 2040, Washington DC., 19 pages (2007).
Leek, C. and Jameson G., "Review of Foamed Bitumen Stabilisation Mix Design Methods", Austroads Technical Report, Austroads Publication No. AP-T178/11, 47 pages (2011).
Maine DOT, "Maine's Experience Utilizing Full Depth Reclamation with Foamed Asphalt", presentation at NESMEA 2004, Portsmouth, NH, 6, pages (2004).
Mallick, R. B., Bergendahl, J. and Pakula, M. "A Laboratory Study on CO2 Emission Reductions through the Use of Warm Mix Asphalt", Transportation Research Board 2009 Annual Meeting, Washington, D.C., 18 pages (2009).
Muthen, K. M., "Foamed Asphalt Mixes: Mix Design Procedure", CSIR TRANSPORTEK Report No. CR-98/077, South Africa, 36 pages (1998).
Namutebi, M. "Some Aspects of Foamed Bitumen Technology", Licentiate Thesis, Division of Highway and Railway Engineering, Department of Transport Science School of Architecture and the Built Environment, Royal Institute of Technology SE100 44 Stockholm, 78 pages (2011).
NCHRP Report 714, "Special Mixture Design Considerations and Methods for Warm Mix Asphalt: A Supplement to NCHRP Report 673: A Manual for Design of Hot Mix Asphalt with Commentary", Transportation Research Board of the National Academies. Washington, DC, 53 pages (2012).
Neu, G.E., "Techniques of Foam Measurement" Journal of Society of Cosmetic Chemists, V.11, No. 7, 390-414 (1960).
Prowell, B.D. "Warm Mix Asphalt: The international technology scanning program summary report", U.S. Department of Transportation, Federal Highway Administration American Association of State Highway and Transportation Officials, National Cooperative Highway Research Program, 21 pages (2007).
Ozturk, H.I. "Quantification of Quality of Foamed Warm Mix Asphalt Binders and Mixtures", Ph.D. Dissertation, Michigan State University, MI, USA, 232 pages (2013).
Ozturk, H.I. and Kutay, M.E., "Effect of Foamed Binder Characteristics on Warm-Mix Asphalt (WMA) Performance", Transportation Research Board 93rd Annual Meeting Compendium Papers, Washington DC, USA, 15 pages (2014).
Ozturk, H.I. and Kutay, M.E., "Sensitivity of Nozzle-Based Foamed Asphalt Binder Characteristics to Foaming Parameters", Transportation Research Board 93rd Annual Meeting Compendium Papers, Washington DC, USA, 22 pages (2014).
Saleh, M., "Characterization of Foam Bitumen Quality and the Mechanical Properties of Foam Stabilized Mixes", 10th International Conference on Asphalt Pavements (ICAP 2006), Quebec City, Canada, 10 pages, (2006).

* cited by examiner $$V^t = h^t p d^2/4$$
$$V_B^t = p d^2/4 \, (h^t - h^f)$$

ASPHALT FOAM COLLAPSE TEST METHODS AND RELATED APPARATUS

CROSS REFERENCE TO RELATED APPLICATION

Priority is claimed to U.S. Provisional Application No. 61/833,232 (filed on Jun. 10, 2013), which is incorporated herein by reference in its entirety.

STATEMENT OF GOVERNMENT INTEREST

None.

BACKGROUND OF THE DISCLOSURE

Field of the Disclosure

The disclosure generally relates to methods and related apparatus for the measurement and determination of the quality of a foamed asphalt binder. Various asphalt binder/foam quality indicators can be measured with the disclosed methods and apparatus, such as bubble size distribution, bubble surface area, foam expansion ratio, foam half-life, foam index, as well as normalized parameters related to the same.

Brief Description of Related Technology

Interest in Warm Mix Asphalt (WMA) technologies in the U.S. has significantly increased since the first trial in 2004 in Florida and North Carolina. WMA mixing temperatures are 20 to 30° C. lower than conventional Hot Mix Asphalt (HMA) and slightly above 100° C. This amounts to about 20-30% reduction in paving temperatures, which leads to numerous benefits. Lower production temperature reduces the energy consumption, leads to lower greenhouse emissions and less aging of the binder. WMA's advantages (e.g., reduced fuel cost and greenhouse emissions) over traditional HMA has made it very appealing to state and local roadway agencies as well as the industry. In 2010, just six years after the first trial in the U.S., 13% of the pavements were constructed with WMA. When fully implemented, reduction in emissions because of the WMA technology is estimated to be equivalent to removing 1.5 million cars every year.

WMA technologies significantly reduce the mixture viscosity at lower temperatures, facilitate coating and increase the workability. WMA also improves the compaction in cold weather, extends the allowable compaction period (increase the haul distance) and potentially more suitable for using high percentage of reclaimed asphalt pavement (RAP). There are currently over 30 different WMA technologies being used throughout the U.S., where about two thirds of the technologies are based on foamed asphalt. In addition, foaming is the most cost effective WMA technology if the long term production is considered. The working principle of most foamers is to introduce air and water into hot asphalt binder (>100° C.) with the help of a spraying nozzle. The water is turned into steam and expands the binder, significantly decreasing the overall viscosity. This aids in aggregate coating, mixture workability and compaction at lower temperatures.

Currently, there are numerous different field and laboratory foaming techniques being used by the industry. The field foaming technologies can be divided into four major types: (I) foaming nozzle-based methods, (II) synthetic zeolite-based methods, (Ill) indirect foaming via mixing hot aggregates with asphalt and wet fine aggregate, and (IV) shear-based mixing. All of these technologies utilize very different methods. For example, in a laboratory foamer, binder flows down in a pipe (via gravity) around an air/water injection nozzle and hits the injected air/water mixture, which creates the steam bubbles. Whereas, in a field method (ASTEC DBG) air/water mixture (at different concentrations) are sprayed into binder to create foam, then the foam is forced through a narrow nozzle before mixing with aggregate.

On the other hand, in Low Emission Asphalt (LEA), coarse aggregate is heated to about 150° C., mixed with (unfoamed) binder along with a coating/adhesion additive. Then, cold wet fine aggregate and recycled asphalt pavement (RAP) are added. While mixing, the moisture in the wet fine aggregate turns into steam and creates the foam.

Because of a wide variety of methods, the resulting WMA mixture is produced at very different conditions (i.e., temperature, water content, asphalt absorption by aggregates, etc.). As a result, parameters affecting WMA pavement performance such as degree of coating, amount of trapped moisture, and asphalt binder absorption onto aggregates may exhibit great variation. However, there is no clear understanding of the effects of different WMA technologies on the quality of the foam generated, which can significantly affect the overall global performance of the mixture. This lack of understanding is partly because there is no standard test method for measuring the characteristics (i.e., the quality) of foamed binders.

SUMMARY

The disclosure relates to asphalt foam collapse test methods and related apparatus for the measurement and determination of foamed asphalt binder quality. Various asphalt binder/foam quality indicators can be measured with the disclosed methods and apparatus, such as bubble size distribution, bubble surface area, foam expansion ratio, foam half-life, foam index, as well as normalized parameters related to the same.

Existing manual techniques for estimating foam expansion ratio (ER) and half-life (HL) involve holding a ruler located on the side of a container filled with foamed asphalt. This is coupled with a timed technician observation of the foam formation and collapse process via stopwatch. This method is neither accurate nor repeatable. Typically only two measurements are taken: (i) volume at the beginning of the foaming (i.e., for initial expansion ratio) and (ii) the time when the height reduced to half of the initial height (i.e., for half-life). As a result, a time-dependent ER curve, which is needed for foam index (FI) calculation, cannot be obtained.

Using the disclosed methods and apparatus, the amount of the foamed asphalt can be measured as a function of time, such as in real time. The resulting time series measurement (e.g., measurement of instantaneous foam amount, volume, height, etc.) can be used to compute various asphalt foam quality indicators such as bubble size distribution, bubble surface area, surface area, index, expansion ratio, half-life and foam index. The foam quality indicators can be used to ensure that a foamed asphalt formed under a given set of conditions has favorable properties to provide a resulting asphalt concrete with desirable physical properties and environmental resistance, for example to calibrate a foaming apparatus and/or to foamed asphalt-aggregate batching process as a function of foam generation conditions.

Thus, the disclosed methods and apparatus permit the repeatable characterization and formation of foamed asphalt compositions, enabling the skilled artisan to form foamed asphalt/aggregate compositions of known, repeatable quality. This enhances the ability to form WMA foamed asphalt concrete with controlled and favorable properties selected for the particular environmental conditions (e.g., climate-, weather-, and/or traffic-related) where the concrete is to be used.

In one aspect, the disclosure relates to a method for determining foamed asphalt quality, the method comprising: (a) providing a foamed asphalt comprising an asphalt medium and a plurality of bubbles dispersed throughout the asphalt medium; (b) allowing the foamed asphalt to decay and measuring the amount of the foamed asphalt as a function of time during decay to provide an amount time series for the decaying foamed asphalt; (c) determining from the amount time series at least one foam quality parameter selected from the group consisting of bubble size distribution parameters, bubble surface area parameters, and combinations thereof; and (d) comparing the foam quality parameter with at least one corresponding foam quality set point.

In another aspect, the disclosure relates to a method for determining foamed asphalt quality, the method comprising: (a) providing a foamed asphalt comprising an asphalt medium and a plurality of bubbles dispersed throughout the asphalt medium; (b) allowing the foamed asphalt to decay and measuring the height of the foamed asphalt along a measurement axis and as a function of time during decay to provide a height time series for the decaying foamed asphalt, wherein the measurement axis is substantially parallel to a decay direction defined by the decaying foamed asphalt; (c) determining from the height time series at least one foam quality parameter; and (d) comparing the foam quality parameter with at least one corresponding foam quality set point.

In another aspect, the disclosure relates to a method for determining foam generation conditions, the method comprising: (a) providing a first foamed asphalt formed at a first set of foam generation conditions; (b) determining foamed asphalt quality for the first foamed asphalt according to any one of the various disclosed methods; (c) providing a second foamed asphalt formed at a second set of foam generation conditions different from the first set of foam generation conditions; and (d) determining foamed asphalt quality for the second foamed asphalt according to any one of the various disclosed methods.

In another aspect, the disclosure relates to a method for forming an asphalt concrete composition, the method comprising: (a) providing a foamed asphalt comprising an asphalt medium and a plurality of bubbles dispersed throughout the asphalt medium; (b) determining foamed asphalt quality for the foamed asphalt according to any of the various disclosed methods; and (c) mixing aggregate with the foamed asphalt to provide the asphalt concrete composition.

In another aspect, the disclosure relates to a method for forming multiple asphalt concrete compositions, the method comprising: (a) performing any of the foregoing methods to form at least two asphalt concrete compositions, wherein: (i) the aggregate has a different characteristic size in each composition; and (ii) the foamed asphalt has a selected different foam quality corresponding to the aggregate characteristic size in each composition.

In another aspect, the disclosure relates to an apparatus for measuring foamed asphalt quality, the apparatus comprising: (a) a vessel for containing a foamed asphalt sample, the vessel defining a foam decay direction; and (b) a means for measuring the height of a foamed asphalt sample in the vessel as a height time series in real time, wherein: (i) the height measuring means defines a measurement axis, and (ii) the height measuring means is positioned remotely from the vessel and such that the measurement axis is substantially parallel to the foam decay direction.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
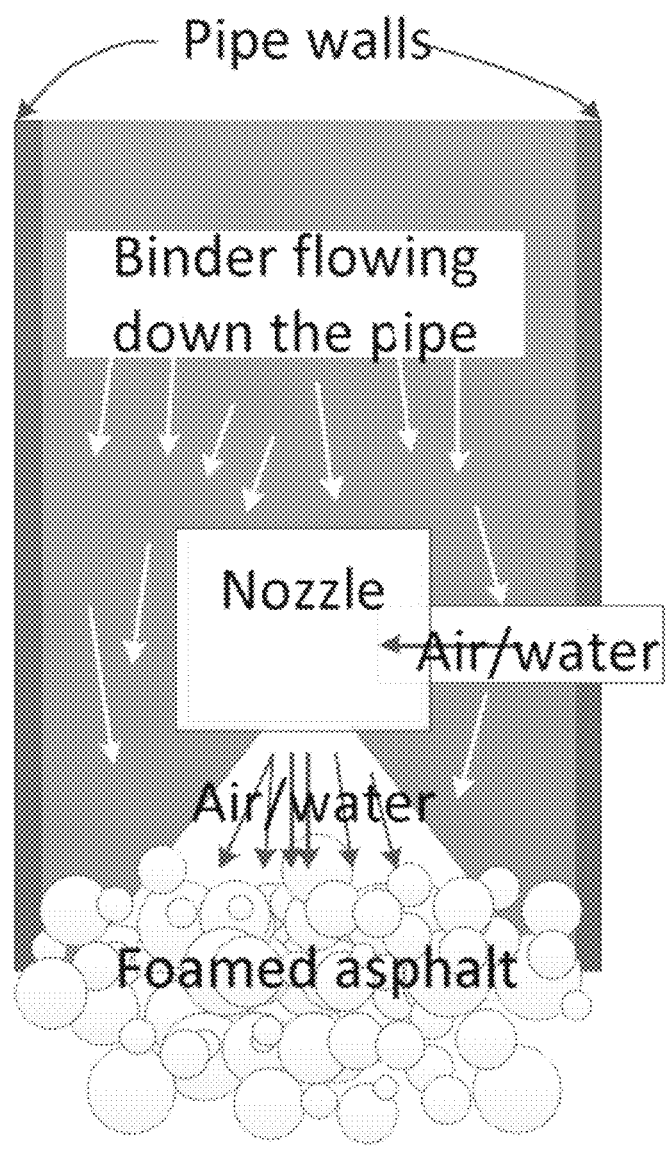
FIG. 1 is a schematic illustrating the working principle of an asphalt foamer apparatus.

While the disclosed methods, apparatus, and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

The disclosure relates to asphalt foam collapse test methods, related apparatus for the measurement and determination of foamed asphalt binder quality, and related compositions including foamed asphalt of known or specified foam quality. FIGS. 5, 6, 7, 13, 14, 15, and 16 illustrate the methods, apparatus, and compositions as described in more detail below. Various asphalt binder/foam quality indicators can be measured according to the disclosure, such as bubble size distribution, bubble surface area, foam expansion ratio, foam half-life, foam index, as well as normalized parameters related to the same. The disclosed methods and apparatus permit the repeatable characterization and formation of foamed asphalt compositions, enabling the skilled artisan to form foamed asphalt/aggregate compositions of known, repeatable quality. This enhances the ability to form WMA foamed asphalt concrete with controlled and favorable properties selected for the particular environmental conditions (e.g., climate-, weather-, and/or traffic-related) where the concrete is to be used.

In one aspect, the disclosure relates to a method for determining foamed asphalt quality, the method including: (a) providing a foamed asphalt 200 including an asphalt medium 210 and a plurality of bubbles 220 dispersed throughout the asphalt medium 210; (b) allowing the foamed asphalt 200 to decay and measuring the amount of the foamed asphalt 200 as a function of time during decay to provide an amount time series for the decaying foamed asphalt 200; (c) determining from the amount time series at least one foam quality parameter selected from the group consisting of bubble size distribution parameters, bubble surface area parameters, and combinations thereof; and (d) comparing the foam quality parameter with at least one corresponding foam quality set point.

In another aspect, the disclosure relates to a method for determining foamed asphalt quality, the method including: (a) providing a foamed asphalt 200 including an asphalt medium 210 and a plurality of bubbles 220 dispersed throughout the asphalt medium 220; (b) allowing the foamed asphalt 200 to decay and measuring the height of the foamed asphalt 200 along a measurement axis M and as a function of time during decay to provide a height time series for the decaying foamed asphalt, wherein the measurement axis M is substantially parallel to a decay direction D defined by the decaying foamed asphalt 200; (c) determining from the height time series at least one foam quality parameter; and (d) comparing the foam quality parameter with at least one corresponding foam quality set point.

Asphalt (alternatively referenced as binder, asphalt binder, asphalt cement, or bitumen) is suitably formed a crude oil/petroleum distillate (heavy fraction). It is a highly viscous, liquid/semi-solid colloidal material including various maltenes in a continuous phase and various asphaltenes (e.g., heteroaromatic polycyclic hydrocarbons) as a dispersed phase. Asphalt can include various additives, such as polymeric materials (e.g., thermoplastic, thermoset), including various elastomers, rubbers, plastomers, etc. The applied methods can be used to characterize foam quality for any of a variety of asphalt compositions, including those specified according to their "performance grade" classification in the general form "PG X Y" as generally understood by the skilled artisan and corresponding to various physical properties of the asphalt. The value for "X" represents the average 7-day maximum pavement design temperature (° C.), and it can include values of 46, 52, 58, 64, 70, 76, or 82° C., as well as any ranges or sub-ranges therebetween. The value for "Y" represents the 1-day minimum pavement design temperature (° C.), and it can include values of −10, −16, −22, −28, −34, −40, or −46° C., as well as any ranges or sub-ranges therebetween.

Various refinements and extensions of the disclosed methods for determining foamed asphalt quality are possible. For example, the asphalt medium 210 can be heated (at least initially) to a suitable warm-mix asphalt temperature, such as at least 105° C., 110° C., or 115° C. and/or up to 115° C., 120° C., 125° C., 150° C., or 175° C. in its initial state and/or throughout the decay process. The bubbles 220 forming the foamed asphalt 200 are generally gas bubbles 220 (e.g., including water and/or air; having a spherical and/or irregular shape), and they can be introduced by any suitable means such as a foaming nozzle, a chemical additive (solid/liquid) transforming to gas upon addition to asphalt medium. The foamed asphalt 200 to be measured for foam quality can exclude or include other additives (e.g., rheology- or property-enhancing additives) and/or aggregate 330.

In further refinements, foam decay or collapse can be performed or observed within an open vessel 100 exposed to the external environment/atmosphere. The foamed asphalt 200 amount as measured during the decay process can be the volume or the height of the foamed asphalt in a sample vessel (e.g., a measured volume time series ($V^t$) or height time series ($h^t$)). The measured time series can represent an absolute amount or a normalized amount, such as the volume or height relative to the initial volume or height prior to measurement/decay (e.g., $V^t/V^o$ or $h^t/h^o$). The measurement of the amount time series is essentially a real-time measurement such as at sampling/measurement rates of at least 0.1 Hz, 1 Hz, 5 Hz, 10 Hz, 30 Hz and/or up to 10 Hz, 30 Hz, 100 Hz, 1000 Hz. A dataset or measurement rate may be sub-sampled to lower rates as desired depending on the characteristic time for a specific decay process.

In further refinements, the foam quality parameter can be a volume-, weight-, area-, or number-based average, mean, or median of a distributed bubble parameter in the foam such as size (e.g., diameter for spherical bubbles or effective/volume-equivalent diameter for non-spherical bubbles) or surface area, or an exact or modeled representation of the (cumulative) distribution itself. Each foam quality parameter can be determined/computed from the amount time series at a selected reference time, such as the initial foamed asphalt state, the final (decayed) asphalt state, or an intermediate time (e.g., $t_m$ for $0 \le m \le 100$ representing a percent volumetric decay of the foamed asphalt from the initial to final states: $V(t_m)=V_o-(m/100) \times (V_{o-Vf})$, such as when $V(t_0)=V_o$, $V(t_{100})=V_f$, and $t_{50}$ is the half life (HL)).

In further refinements, the foam quality parameter can be selected from the group consisting of bubble size distribution parameters, bubble surface area parameters, integral decay properties, characteristic decay times, and combinations thereof. An integral decay property can include the time integral over length in time of the decay process for the measured height or corresponding variable such as foam volume (e.g., foam index (FI; $\int ER(t)dt$) or analogous corrected foam index based on expansion ratio (ER) but excluding contribution from asphalt binder volume (e.g., $\int [ER(t)-1]dt$)). A characteristic decay rate can include $t_m$ as defined above, such as $t_{50}$ for the half-life (HL).

In an embodiment, at least one foam quality parameter is a bubble size distribution parameter. For example, (i) the bubble size distribution parameter can be an average bubble size (e.g., $D_{50}$; optionally normalized relative to a selected characteristic aggregate size to be added to the asphalt binder) of the distribution of bubbles prior to measuring the amount of the foamed asphalt as a function of time, and (ii) the corresponding foam quality set point can be selected from the group consisting of a minimum, a maximum, or a range for the average bubble size. More generally, the bubble size/diameter distribution parameter can be a diameter $D_n$ of the cumulative distribution (e.g., $0<n<100$ where n represents the percent undersize (cut size), such as $D_{10}$, $D_{30}$, $D_{50}$ (average/median), $D_{60}$, $D_{90}$), a representation of distribution width (e.g., $D_{n1}/D_{n2}$ for different cut sizes such as the foregoing), and/or a mean ($\mu$) and/or standard deviation ($\sigma$) for an equivalent normal or log-normal distribution representing the size distribution. The bubble size/diameter distribution parameter can be a normalized parameter, such as normalized with a characteristic size of the intended aggregates for use with foamed binder (e.g., $D_n^*$ of cumulative aggregate distribution analogous to the same or similar bubble distribution parameter, such as a normalized ratio $D_{50}/D_{50}^*$).

In an embodiment, at least one foam quality parameter is a bubble surface area or bubble volume parameter. For example, the bubble surface area parameter can be a normalized total surface area of all bubbles present in the foamed asphalt prior to measuring the amount of the foamed asphalt as a function of time. More generally, the bubble area or volume parameter can be a total absolute or normalized surface area or volume of all bubbles or a representation of the bubble area or volume distribution, for example $A_{bubble,n}$ or $V_{bubble,n}$ analogous to $D_n$ for bubble size (e.g., with any of the various cut-sizes, distribution widths, or distribution fit parameters described above for the diameter).

In further refinements, each measured foam quality parameter can be compared with one or more corresponding set points/quality criterion generally in the form of an acceptable minimum, maximum, or range for the particular foam quality parameter. For example, an absolute or normalized $D_{50}$ of the bubble size distribution (or other parameter) greater than a set point minimum, less than a set point maximum, and/or within a set point range can be determined to be suitable for an intended use based on the set point. Alternatively, a parameter that is greater than a set point maximum, less than a set point minimum, and/or outside a set point range can be determined to be unsuitable for an intended use based on the set point. In various refinements, set points can be selected as a function of the asphalt binder (e.g., physical properties thereof) and/or of intended use (e.g., aggregate to be used, environmental/traffic conditions in area of resulting asphalt concrete use).

Figure 13:
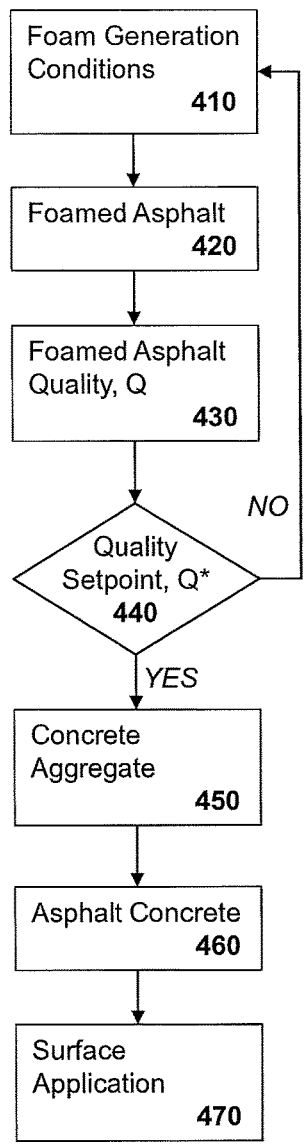
FIG. 13 is a flowchart illustrating a method according to the disclosure for determining suitable asphalt foam generation conditions and the formation of an asphalt concrete composition using the generated foam.

In further refinements, the methods for determining foamed asphalt quality can be extended to an iterative process generating new/different foamed asphalts for evaluation if one or more foam quality set points are not met (e.g., repeating the quality determination methods for the new foamed asphalt). As illustrated in FIG. 13, for example, (first) foam generation conditions 410 are selected and used to form a (first) foamed asphalt 420 (e.g., using a foaming apparatus at the selected foam generation conditions). The foamed asphalt 420 is then evaluated according to the disclosure to determine a foamed asphalt quality parameter Q at 430, which is compared with a foam quality setpoint Q* at 440. If the measured foamed asphalt quality parameter Q meets the setpoint Q* (e.g., to with a preselected tolerance), the foamed asphalt 420 can be combined with concrete aggregate 450 to form an asphalt concrete composition 460, which can be applied to a surface 470 as desired in normal use. If the measured foamed asphalt quality parameter Q does not meet the setpoint Q*, a new (second) set of foam generation conditions 410 are selected and used to form a (second) foamed asphalt 420, the quality Q of which can be tested at 430. The process can be iteratively performed for one or more different quality parameters (e.g., $Q_i$ for i=1 to n different parameters) until a foamed asphalt 420 meeting all desired quality parameters is formed and combined with aggregate 450 to form an asphalt concrete composition 460.

Figure 14:
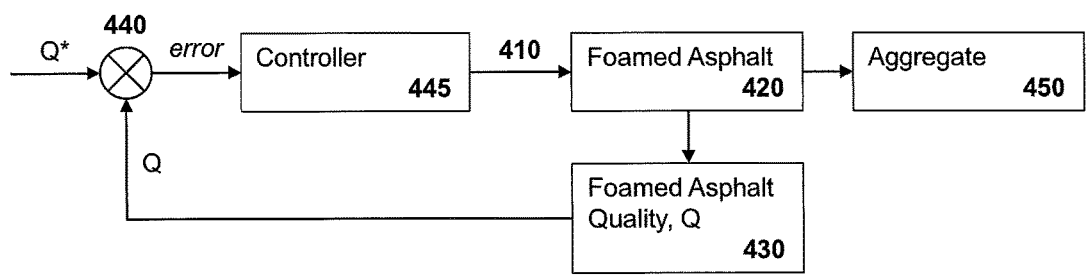
FIG. 14 illustrates a feedback control process for forming an asphalt foam meeting a specified foam quality setpoint.

In further refinements, the methods for determining foamed asphalt quality can be extended to methods of manufacturing a foamed asphalt-aggregate mixture for laying asphalt concrete if foam quality set points are met (e.g., as a quality control check on the foamed asphalt-aggregate mixture, such as in an iterative process to form a foamed asphalt binder of acceptable quality). As illustrated in FIG. 14, for example, the general process of FIG. 13 can be performed with a feedback control loop (e.g., as part of an automated control process implemented by a suitably programmed computer). The comparison of the setpoint Q* and the actual quality Q of a particular foamed asphalt 420 sample can provide the error input to a suitable electronic controller 445 (e.g., a P, PI, PD, or PID controller) which generates a new set of foam generation conditions 410. In some embodiments, the foamed asphalt 420 is combined with the aggregate 450 only after the foam quality Q is sufficiently close to the setpoint Q*. In other embodiments, the majority of the foamed asphalt 420 is continuously (e.g., periodically on a continuous basis) combined with the aggregate 450, and a portion of the foamed asphalt 420 is continuously (e.g., periodically on a continuous basis) sampled and tested at 430 to determine current asphalt quality Q, which can be adjusted as desired via the control loop to drive the steady asphalt quality Q towards its setpoint value Q*.

When measuring height as an amount time series, the measurement axis M can be a primary (or initial) direction along which the height of moving/decaying foamed asphalt interface 230 is measured/detected, for example a vertical direction for a physical marker 150 floating on the foam surface 230 or a path of travel for an electromagnetic radiation-based height detection means (e.g., optical detection such as using reflected laser light). The decay direction D can be represented by a surface-normal direction defined by the external/exposed asphalt binder surface 230 moving during decay (e.g., translating downwardly). The measurement axis M and decay direction D can be (substantially) parallel or collinear, for example within 5°, 10°, 15°, 20°, 30°, 45°, or 60° of each other. In various embodiments, the height time series can be correlated to volume or amount time series for determination of the foam quality parameter(s) of interest (e.g., based on the geometry of the vessel 100).

In a refinement, the methods can further include adding a buoyant marker 150 to an external surface 230 of the foamed asphalt 200, wherein measuring the height (or other amount) of the foamed asphalt 200 includes measuring the height (or other property or positional characteristic) of the buoyant marker 150. The buoyant marker 150 is suitably selected as any conveniently shaped solid object (e.g., spherical) such that its density is less than that of the foamed asphalt 200 (i.e., $\rho_{marker}<\rho_{foam}$) at the most expanded (i.e., lowest density) foam state. The density difference can be based on the natural density of the marker 150 or based on an effective marker density as offset by a mass/force 170 acting in a direction opposing the gravitational force on the buoyant marker 150. In some embodiments, the marker 150 can be coated with a layer of asphalt (e.g., a dried/cured layer of the same or different asphalt being measured for foam quality). In a further refinement, the buoyant marker 150 is sufficiently sized to reduce erratic movement of the buoyant marker 150 resulting from bubbles 220 escaping from the foamed binder 210 during decay. Suitably, the buoyant marker 150 has a characteristic size (e.g., diameter D or other characteristic length/width in a plane perpendicular to the air-foam interface/direction of bubble movement) sufficiently large relative to the size of the escaping bubbles 220 (e.g., ratio of marker characteristic size relative to initial mean bubble size $D_{marker}/D_{50,bubble}$ of at least 1, 2, 5, 10, or 20). The characteristic size is suitably small enough to permit sufficient open area for bubble escape/foam decay (e.g., such as occupying not more than 50%, 20%, 10%, or 5% of the total exposed area that would otherwise be available for bubble escape).

In another aspect, the disclosure relates to a method for determining foam generation conditions, the method including: (a) providing a first foamed asphalt 200' formed at a first set of foam generation conditions; (b) determining foamed asphalt quality for the first foamed asphalt 200' according to any one of the various disclosed methods; (c) providing a second foamed asphalt 200" formed at a second set of foam generation conditions different from the first set of foam generation conditions; and (d) determining foamed asphalt quality for the second foamed asphalt 200" according to any one of the various disclosed methods.

Various refinements and extensions of the disclosed methods for determining foam generation conditions are possible. For example, the foam generation conditions can include one or more independent variables that can be changed when generating/creating a foam, in particular those which may affect the formation of dispersed bubbles 220 in the asphalt medium 210. Non-exhaustive examples of foam generation conditions include: asphalt temperature upon foaming, relative amount and/or pressure of air and/or water introduced into asphalt to generate foam, apparatus used for foaming (e.g., injection nozzle selection/geometry), loading/use of chemical foaming asphalt additives, type of asphalt medium, presence/absence/amount of non-foaming asphalt additives, etc. In an embodiment, the method can be iteratively (e.g., conditionally) repeated if the first foamed asphalt quality does not meet one or more of the set points (e.g., which are suitably the same for first, second, and subsequent asphalts) and/or until all set points are met. In another embodiment, the method can be arbitrarily (e.g., unconditionally) repeated for a selected set of foam generation conditions, for example to generate a optimization or calibration map, table, library, etc. establishing the relationship of one or more foam quality parameters to one or more foam generation conditions, such as for a given asphalt medium.

Figure 15:
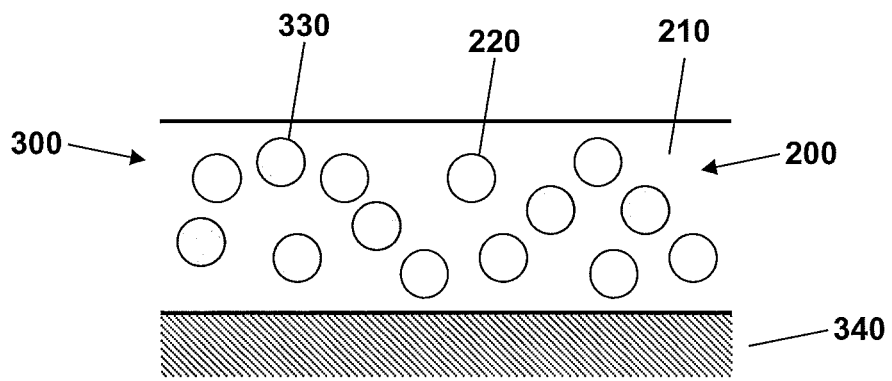
FIG. 15 illustrates an asphalt concrete composition according to the disclosure as applied to a roadway or other surface.
Figure 16:
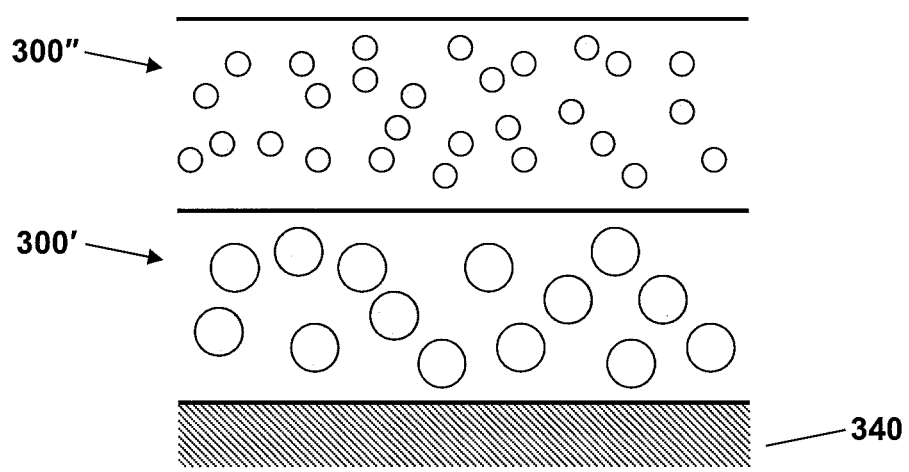
FIG. 16 illustrates an asphalt concrete composition according to the disclosure as a bilayer structure having different foam quality characteristics and/or aggregate size distribution characteristics in each layer.

In another aspect, the disclosure relates to a method for forming an asphalt concrete composition 300, the method including: (a) providing a foamed asphalt 200 including an asphalt medium 210 and a plurality of bubbles 220 dispersed throughout the asphalt medium 210; (b) determining foamed asphalt quality for the foamed asphalt 200 according to any of the various disclosed methods; and (c) mixing aggregate 330 with the foamed asphalt 200 to provide the asphalt concrete composition 330 (e.g., which may be subsequently applied to a roadway or other surface 340 as illustrated in FIG. 15).

Various refinements and extensions of the disclosed methods for forming an asphalt concrete composition 300 are possible. For example, the foamed asphalt quality determination can be performed online as part of an asphalt concrete 300 batching process in which a sample of a foamed asphalt 200 batch is tested either before, while, or after the remainder of the foamed asphalt 200 is mixed with the aggregate 330 as a quality control check for the asphalt concrete 300 batch (e.g., where the batch can be rejected or modified prior to surface application if it fails at least one quality set point). Alternatively or additionally, the foamed asphalt quality determination can be based on selection of a set of previously established foam generation conditions for the specific asphalt binder 210, means for generating foam (e.g., apparatus), and intended use of the asphalt concrete 300.

In a refinement, the aggregate 330 can be selected from stone, gravel, sand, and combinations or mixtures thereof. The aggregate 330 can be classified/selected according to an aggregate characteristic size, which can correspond, for example, to the largest, median, or smallest size particle in the aggregate particle size distribution, such as 37.5 mm (1.5 in sieve passing), 25.0 mm (1 in), 19.0 mm (0.75 in), 12.5 mm (0.5 in), 9.5 mm (0.375 in), 4.75 mm (No. 4), 2.36 mm (No. 8), 1.18 mm (No. 16), 0.60 mm (No. 30), 0.30 mm (No. 50), 0.15 mm (No. 100), 0.075 mm (No. 200), or ranges therebetween, based on standard sieve sizes/techniques. In another refinement, (i) the asphalt medium 210 is present in an amount ranging from 2 wt. % to 10 wt. % relative to the asphalt concrete composition 300 (e.g., at least 2 wt. %, 3 wt. %, or 4 wt. % and/or up to 5 wt. %, 6 wt. %, 8 wt. %, or 10 wt. %); and (ii) the aggregate 330 is present in an amount ranging from 90 wt. % to 98 wt. % relative to the asphalt concrete composition 300 (e.g., at least 90 wt. %, 92 wt. %, 94 wt. %, or 95 wt. % and/or up to 96 wt. %, 97 wt. %, 98 wt. %).

In another aspect, the disclosure relates to a method for forming multiple asphalt concrete compositions 300', 300", the method including: (a) performing any of the foregoing methods to form at least two asphalt concrete compositions 300', 300", wherein: (i) the aggregate 330 has a different characteristic size in each composition 300', 300"; and (ii) the foamed asphalt 200 has a selected different foam quality corresponding to the aggregate characteristic size in each composition 300', 300". In a related embodiment, the multiple compositions 300', 300" can be used to lay sequential layers of asphalt concrete on a roadway or other surface 340, where the foamed asphalt is custom-selected for the aggregate in each layer (e.g., to enhance aggregate coating) and/or for the relative vertical position of each layer in a composite laminate concrete structure (e.g., to enhance foam dissipation and prevent trapped moisture in a cooled asphalt concrete). As qualitatively illustrated in FIG. 16, the lower asphalt concrete layer is formed from a composition 300' having larger characteristic bubble and aggregate sizes relative to the upper asphalt concrete layer formed from a composition 300" having smaller characteristic bubble and aggregate sizes, although the relative bubble and/or aggregate sizes may be switched in various embodiments. In various embodiments, the bubbles 220 from a lower applied composition (e.g., composition 300' in FIG. 16) are permitted to dissipate (e.g., partially, completely, or substantially completely to reduce or eliminate trapped moisture such as from water-based bubbles or otherwise) prior to application of an upper applied composition (e.g., composition 300" in FIG. 16). In other embodiments, the composite compositions 300', 300" are sequentially applied to a surface 340 or an underlying asphalt composition without substantial time for bubble 220 dissipation in the underlying layer. In such cases, bubbles 220 from the lower layers travel through multiple asphalt composition layers before release and dissipation into the external environment. Absent the bubbles 220, FIG. 16 similarly can represent a bilayer structure for cooled asphalt concrete formed after bubble dissipation from all layers.

In another aspect, the disclosure relates to an apparatus 10 for measuring foamed asphalt quality, the apparatus 10 including: (a) a vessel 100 for containing a foamed asphalt 200 sample, the vessel 100 defining a foam decay direction D; and (b) a means 140 for measuring the height of a foamed asphalt 200 sample in the vessel 100 as a height time series in real time, wherein: (i) the height measuring means 140 defines a measurement axis M, and (ii) the height measuring means 140 is positioned remotely from the vessel 100 and such that the measurement axis M is substantially parallel to the foam decay direction D. The foam decay direction D can be defined along a central axis of the vessel 100, or perpendicular to a vessel 110 open area through which bubbles can escape during foam decay in an open vessel 100. Being positioned remotely can reflect a spatial relationship in which the height measuring means 140 is remote from/not connected to a vessel 100 wall, positioned externally to the vessel 100, and/or above the position of a moving external surface 230 of a decaying foamed asphalt 200 sample when present (e.g., at least one component of the height measuring means 140 can be positioned externally to the vessel 100 and at least one component of the height measuring means 140 can be above the position of the moving external surface 230 of the decaying foamed asphalt 200 sample).

Various refinements and extensions of the disclosed apparatus 10 for measuring foamed asphalt quality are possible. For example, the height measuring means 140 can include a first buoyant marker 150 positionable within the vessel 100 (e.g., positionable within an interior volume V defined by the vessel 100 but not necessarily in contact with the vessel 100, such as on a top surface 230 of a foamed asphalt 200 sample therein). In a further refinement, the height measuring means 140 can further include a second marker 160 spatially coupled to the first buoyant marker 150. The second marker 150 can be positioned remotely from or external to the vessel 100. Spatial coupling permits spatial displacement of the second marker 160 to be correlated to a corresponding displacement of the first buoyant marker 150 and/or the volume/height of foamed asphalt 200 in the vessel 100. The first buoyant marker 150 and second marker 160 can be physically connected, such as with a line, wire, string, etc. or other physical connecting means 145. Suitably, the physical connecting means is (relatively) transparent and/or substantially the same color as a background color of the apparatus 10 to facilitate automated optical detection of the second maker 160 with minimal optical interference from the connecting means 145. In an embodiment, the physical connecting means 145 is under tension with the first buoyant marker 150 coupled thereto at or near one end of the physical connecting means 145, a counter weight 170 coupled thereto at or near an opposing end of the physical connecting means 145, and the second marker 160 coupled thereto at a position intermediate the first buoyant marker 150 and the counter weight 170. In a refinement, the first buoyant marker 150 is coated with an asphalt binder (e.g., to limit or prevent further absorption of binder by the first buoyant marker 150, which could otherwise alter the selected balance (or slight desirable imbalance) established by the counter weight 170). In another refinement, the height measuring means 140 further includes a means for measuring at least one of translational or rotational movement corresponding to movement of the first buoyant marker 150 (e.g., translational movement reflected by the second marker 160; rotational movement reflected by a pulley 157/shaft 155 coupled to the first buoyant marker 150 with a physical connecting means 145). For example, a shaft encoder (or other electro-mechanical device for detecting angular position of a shaft or axle) can be used to detect and measure rotational movement of the pulley 157 and/or shaft 155, which can be correlated to translational movement of the first buoyant marker 150 and/or the second marker 160. In another refinement, the height measuring means 140 further includes a means for optically measuring spatial displacement of the second marker 160 (e.g., a video camera, for example coupled to a computer for acquiring, storing, and/or analyzing time series data for the second marker 160).

EXAMPLES

The following examples illustrate the disclosed methods and apparatus, but they are not intended to limit the scope of any claims thereto.

This example illustrates a testing apparatus, referenced as the Asphalt Foam Collapse Test (AFCT or AFCT apparatus), to measure parameters that indicate the quality of foamed WMA binder. The AFCT measures the reduction in height of the foamed binder as it collapses, using a low-cost image acquisition system and relatively simple image analysis technique. The AFCT was used to measure and evaluate various potential quality indicators such as Expansion Ratio (ER), Half-Life (HL), and Foam Index (FI). In addition, this example determines the Bubble Size Distribution (BSD) of the bubbles in the foamed WMA binders. The BSD is then used to evaluate a parameter, called Surface Area Index (SAI), as an indicator of foamed binder quality. The SAI is a dimensionless parameter that is the ratio of total surface area of all bubbles to the surface area of the binder in a cylindrical container once the foam completely dissipates. The data illustrates that SAI is a strong candidate for evaluating foamed WMA binder for coating and workability. Furthermore, this example examines the effect of water content and air nozzle pressure on the foam properties. Results revealed that the water content and air pressure have significant influence on ER, HL, FI, BSD and SAI. It was observed that the low water content and low pressure produced foams with smaller bubbles as compared to foams made with high water content and pressure, which affected the aggregate coating.

Figure 2:
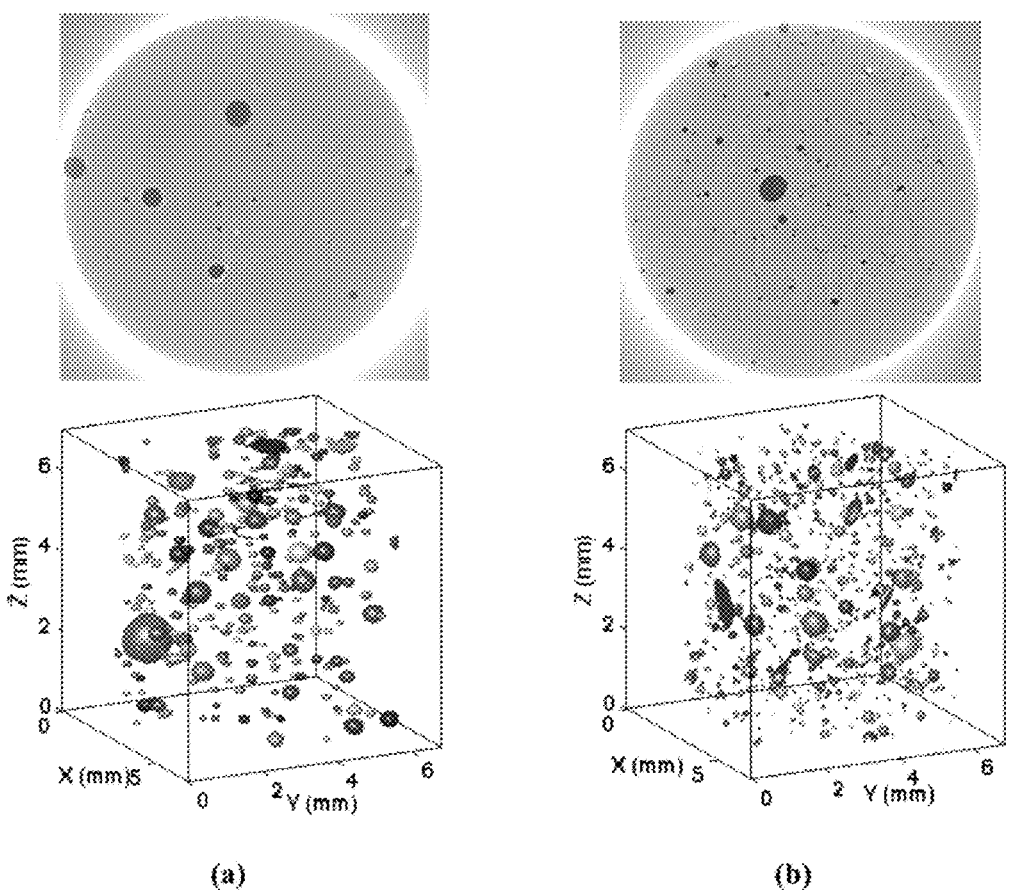
FIG. 2 is a schematic visualization of bubbles in two different types of foamed binders generated by image analysis of 3D XRM images: (a) PG58-28 unmodified binder, and (b) PG 70-22 ELVALOY modified binder. Grayscale images in the top are 2D slices of the XRM images, where dark spherical areas are bubbles, grey areas are asphalt binder.

Foam Characterization: Foams in different disciplines are typically classified as Type-1 and Type-2. Type-1 foams have well separated spherical bubbles in the liquid, where the liquid volume is the same or larger than the bubbles. This type is also known as Kugelschaum or wet foam, gas emulsion or ball foam. Type-2 foams have non-spherical (polyhedral) bubbles separated by almost flat liquid films called lamellae. Foamed asphalt used in most WMA applications probably cannot be classified into just one of these types. Depending on the technology, foamed WMA can be a combination of Type-1 and Type-2 foams. Jenkins (2000) suggested that the foamed asphalts used in base stabilization applications are closer to Type-2 foam. However, Kutay and Ozturk (2012) showed that the bubbles in foamed WMA binders made using a laboratory foamer are spherical and similar to Type-1 as shown in FIG. 2. FIG. 2 shows X-ray Microtomography (XRM) images of two different foamed binders where the bubbles are clearly spherical (i.e., Type-1). FIG. 2 also shows that the PG70-22 ELVALOY modified binder has a lot more small bubbles as compared to the PG58-28 unmodified binder. Both of these binders were prepared in the same conditions (e.g., temperature, water content and air pressure). It is noted that the 3D XRM imaging of the foamed binders shown in FIG. 2 was accomplished by instantly freezing the foam using liquid nitrogen right after it was generated.

Typical tests for characterization of foams can be divided into three major categories: (i) lifetime of individual bubbles, (ii) static foam tests and (iii) dynamic foam tests. The measurement of bubble lifetime is not commonly used since small contaminations and vibrations influence the results and reproducibility is not good. In static foam tests, typically a constant volume of foaming solution in a pipette is allowed to fall a specified distance into a separate volume of the same solution that is contained in a vessel. Decay of the volume of the foam as well as the initial volume (right after draining of the fluid above) is measured (ASTM D1173-53: Ross and Miles Test). There are simpler tests such as ASTM D3601-88 (Bottle Test) and D3519-88 (Blender Test), which are also variations of the static foam tests where reduction in height of the foam over time is measured. The main difference is how the foam is generated. In dynamic foam tests, foam is generated by flowing gas through a porous orifice into the fluid. The volume of the foam is measured when steady-state flow is achieved. Examples of such tests include ASTM D892-74 and D1881-86. It should be noted that unlike foams in many other disciplines, there is typically no static foam layer on the surface of the binder in foamed WMA applications. The bubbles rising to the surface typically collapse and disappear. Therefore, dynamic foam tests are probably not applicable to foamed WMA binders.

In most of the ASTM tests described above, the foaming characteristics of the fluid are measured and the foaming method is kept constant (e.g., pushing air through the porous stone). However, there are various methods of making foam in WMA applications. Therefore, the test method for foamed WMA should be such that the foamed WMA specimen sampled at the plant or from a laboratory device is measured and compared to a baseline method. For this, some kind of static foam test is needed, where the reduction in height of the overall foamed asphalt is measured. Then this can be used to calculate parameters such as expansion ratio and half-life.

The NIBEM-T foam stability instrument is an apparatus typically used to measure the reduction in foam height of beers. In this system, a movable plate with three electrodes is lowered to make contact with the surface of the foam. As the foam collapses, contact between the electrodes and the foam is lost. The instrument continuously moves the plate down to restore contact. The measured rate at which the plate is lowered quantifies the rate of collapse of the foam. However, in its present configuration, this system has operation temperature range between −5° C. and 40° C., which will not allow testing of foamed WMA.

Neu (1960) presented various methods of foam measurement and defined several parameters to characterize foam. The focus of this research was on the foams generated by shampoo and toothpaste. A method assessing the foaming profile included parameters such as (i) Specific Foam Volume (ml/g), (ii) Density=Mass of Foam/Volume, (iii) Viscosity=measured using Modified Techne Viscometer, (iv) Light Transmission: The loss of light transmission through a layer of foam is a function of the degree of dispersion of air, (v) Photomicrography: The particle size distribution and specific surface area of the foam measured on a 100 cm² area, and (vi) Foam Drainage. Among these methods, most appropriate parameters that may apply foamed WMA are probably the particle (bubble) size distribution and specific surface area.

Saleh (2006) used a Brookfield viscometer to measure the change in viscosity of the foamed asphalt with time. As an alternative measure of the quality of the foamed asphalt, he suggested that the average foam viscosity over the first 60 seconds of foaming could be used. It should be noted that foams are typically non-Newtonian fluids. Therefore, their viscosity depends on the applied shear rate. Also, steady-state shearing motion is needed to measure a correct viscosity. It is important to evaluate the repeatability and accuracy of viscosity measurements in highly dynamic (unsteady) foamed asphalt, which typically collapses quickly. While the method may be promising, care should be taken while defining and interpreting the viscosity measurements.

Several parameters were introduced for characterization of asphalt foams used in base stabilization applications. One of them is the expansion ratio (ER), which is the ratio of the expanded volume to the initial volume of the binder. The dissipation of moisture, on the other hand, is typically quantified using the parameter called half-life. The half-life is defined as the elapsed time between the time at which the foamed binder reaches its maximum volume and the time it reaches to half of the maximum volume. Brennen et al. (1983) noted that the expansion ratio and half-life are affected by the amount of foamed asphalt prepared, water content used and the temperature at which the foaming took place. Typically expansion ratio increases with foaming temperature and water content; whereas, half-life decreases with increasing temperature and water content. Leek and Jameson (2011) recommended the ER to be between 8 and 20 and the half-life to be minimum 6 seconds for foams used in base stabilization applications. Foam Index (FI), the area under the ER versus time curve, is another parameter introduced by Jenkins (2000). These parameters were originally developed for base stabilization application where the binder content is much less (2-3%) than WMA (4-6%). As a result, their applicability to WMA needs to be investigated.

Figure 3:
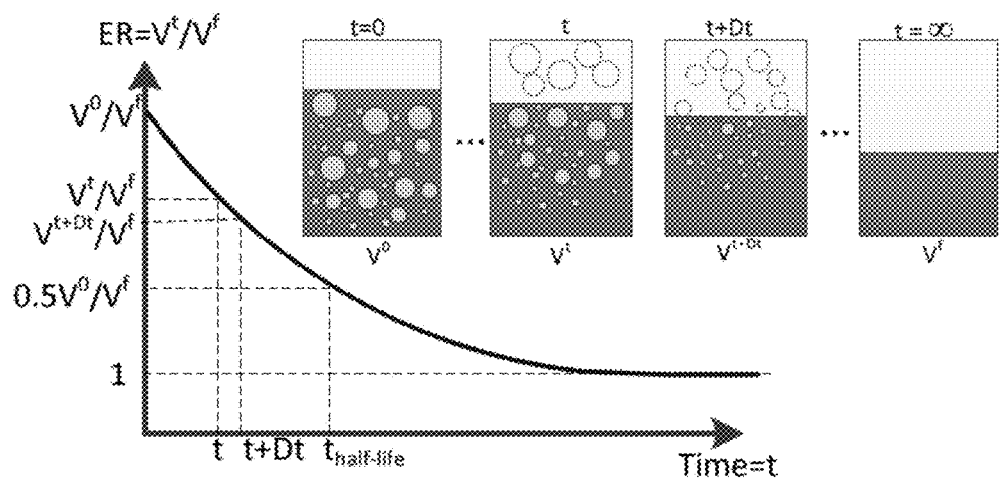
FIG. 3 is a graph illustrating a representative expansion ratio (ER) versus time (t) curve ($V^t$ is overall foam volume at time t; inset schematics illustrate bubble transport and foam decay over time).

Expansion Ratio, Half-Life and Foam Index: FIG. 3 shows an illustration of reduction in Expansion Ratio (ER) with time, which is equivalent to reduction in height of a foamed binder with time. The ER can be defined according to Equation (1), where $V^0$ and $V^f$ are overall foam volume at time t=0 and final binder volume after all foam dissipates, respectively (see FIG. 3). The ER is a measure of volume of the steam bubbles. The half-life (HL), on the other hand, represents the rate of dissipation of the foam and can be defined according to Equation (2), where $t_{0.5V0/Vf}$ is the time at which the overall foam volume is reduced by half, as shown in FIG. 3 ($t_{0.5V0/Vf}=t_{half-life}$ in FIG. 3).

$$ER = \frac{V^0}{Vf} \quad (1)$$

$$HL = t_{0.5V^0/Vf} \quad (2)$$

Foam Index (FI) is defined as the area under the ER versus time curve and it is a measure of a combination of ER and half-life (Jenkins 2000). The FI can be calculated via a discrete integration according to Equation (1), where FI is the Foam Index, $ER_t$ and $ER_{t+1}$ are the expansion ratios at times t and t+1, respectively.

$$FI = \sum_{t=0}^{t_{ER=1}} 1/2(ER_t + ER_{t+1}) \times (t_{t+1} - t_t) \quad (3)$$

Jenkins (2000) described a procedure to measure the ER at different times and recommended that the height measurements of the foamed asphalt should be taken in 10 second intervals. Even though it is not mentioned and investigated in Jenkins (2000), FI is an indirect indicator of the total surface area of the bubbles. The bubble size distribution as well as the total surface area of the bubbles can be computed from the ER versus time data.

Expansion ratio and half-life are typically measured with the aid of ruler located on the side of a container filled with foamed asphalt. This is coupled with a timed technician observation of the foam formation and collapse via stopwatch. This method is both simple and practical, however it is not very accurate and repeatable (. Typically only two measurements, volume at the beginning of the foaming (for expansion ratio) and the time when the height reduced to half of the initial (for half-life) are taken. As a result, the time dependent ER curve, which is needed for Foam Index (FI) calculation, cannot be obtained. Namutebi (2011) used a video camera to capture the images of the foamed asphalt in a container during collapse of the bubbles with the aid of a dipstick with marks. However, the method was only used to collect data to measure the ER and half-life and the entire ER versus time data was not measured. He and Wong (2006) utilized a video camera to record the foam generation and dissipation process. Then, they visually determined the height values at different times from the recorded video and generated ER versus time graphs.

In WMA applications, half-life and expansion ratio may be important parameters that indirectly relate the workability and coating, respectively. For example, if the half-life is long (i.e., the foam collapses in a long period of time), overall viscosity of foam will remain relatively low and good workability can be expected. On the other hand, the expansion ratio is an indicator of total volume of bubbles. It can be claimed that as the bubble volume increases, the surface area will also increase. However, the expansion ratio (ER) cannot provide the size distribution of the bubbles, which is very important for surface area calculation. High surface area is desirable because more surfaces will be available for fine and coarse aggregates for better coating. Table 1 shows a comparison of surface areas of several bubbles with different sizes. All have the same total bubble volume (i.e., 523.6 mm3), which would lead to same expansion ratio if they were in a foamed binder. However, since surface area is inversely related to the radius, when the radius reduced from 5 mm to 0.25 mm, the total surface increased 20 times (even though volume, i.e., ER is same).

TABLE 1

Comparison of surface areas of bubbles with different sizes

|  | Number of bubbles (n) | | | |
| --- | --- | --- | --- | --- |
|  | 1 | 125 | 1000 | 8000 |
| Radius (R), mm | 5.00 | 1.00 | 0.50 | 0.25 |
| Volume ($V_B$ = n * 4/3 $\pi R^3$), mm$^3$ | 523.6 | 523.6 | 523.6 | 523.6 |
| Surface area ($S_B$ = n * 4$\pi R^2$), mm$^2$ | 314.2 | 1570.8 | 3141.6 | 6283.2 |
| Surface area ratio (with respect to R = 5 mm), i.e., $S_B/S_{B(R=5\ mm)}$ | 1 | 5 | 10 | 20 |

It should be noted that the small bubbles will collapse much slower than large bubbles, which may affect the long term performance of the pavement if encapsulated small moisture bubbles exist after the pavement construction. Therefore, an optimum size range should be specified in foamed WMA applications.

Bubble Size Distribution: The Bubble Size Distribution (BSD) as well as the Bubble Surface Area (BSA) are very important parameters, since they can directly influence the ability of the foamed binder to coat the aggregates. As the surface area of the bubbles increase, more interfaces are available for interaction of binder and aggregates. As a result, better coating can be achieved. It has been already mentioned that small-size bubbles collapse (or dissipate) much slower than large size bubbles, which leads to longer half-life. This can potentially aid in workability during placement and compactability. However, there is a danger that encapsulated moisture bubbles remaining after construction may lead to moisture damage. Therefore, an optimum size range, or an optimum surface area range should be defined.

Theoretically, BSD can be computed from the rate of reduction of the volume of the foam with time. This is accomplished by using the Stoke's law (Lamb 1932), similar to the method used in the traditional Hydrometer test, which is commonly used in Geotechnical engineering for measurement of grain size distribution of the fine soils. One major difference is that the Hydrometer apparatus is not used since it is not practical because of the high temperature of the foamed binder and its opaque nature. A method to measure the reduction in the volume of the foamed asphalt is presented below. Once the BSD is computed, total surface area of the bubbles can be computed.

Figure 4:
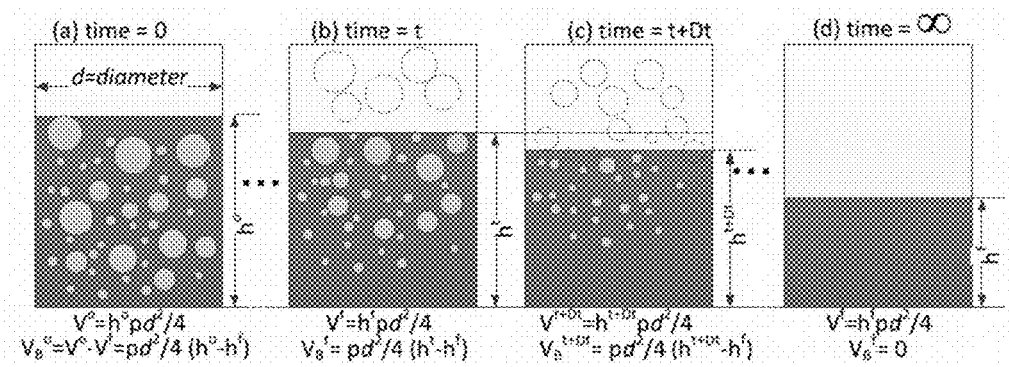
FIG. 4 is a schematic illustrating the reduction of foamed binder volume with time. In the figure, $V^o$ is the total volume of foam (binder+bubbles) at t=0, $V_B^o$ is the volume of bubbles at t=0, and $V_f$ is the volume of binder (when there is no bubble phase).

FIG. 4 shows an illustration of rising and collapse of the bubbles in a cylindrical container and, as a result, reduction in overall height of the foamed binder. It is well known (based on Stoke's law) that the bubbles with large volume (diameter) will rise to the surface faster than those with smaller diameter. Stoke's law for rising bubbles in a fluid can be expressed according to Equation 4 (Lamb 1932), where v=velocity of bubble (m/s), g=gravitational acceleration (9.81 m/s$^2$), D=diameter of bubble (m), $\rho_f$=density of fluid (kg/m$^3$), $\rho_b$=density of bubble (kg/m$^3$), µ=dynamic viscosity of the fluid (Pa·s=kg/(m·s)). Equation 4 shows that if the velocity of a bubble rising in a fluid is known, its diameter is calculated using the density and viscosity of the fluid (bubble density may be neglected since it is much lower than the fluid density).

$$D = \sqrt{\frac{18\mu v}{(\rho_f - \rho_b)g}} \quad (4)$$

In order to calculate the average diameter of bubbles escaping within a time interval (Δt), average velocity of the bubbles is needed. At any time interval Δt, the rate of reduction of the height of the foamed fluid is the same as the average velocity of the bubbles escaped within that time interval. Average velocity can be obtained from the reduction in height of the foamed fluid in the container according to Equation 5, where v$^t$=average velocity of the bubbles escaped at time t, Δt=time interval, h$^t$ and h$^{t+\Delta t}$ are the height of the foamed fluid at t and t+Δt, respectively.

$$v^t = \frac{h^t - h^{t+\Delta t}}{\Delta t} \quad (5)$$

For the foamed binder in FIG. 4, percentage of the bubbles escaped (PBE) from the binder (i.e., bubbles that have risen to the surface) at an intermediate time ($\Delta t$) interval can be obtained according to Equation 6, where $PBE^t$=percentage of bubbles escaped at time interval $\Delta t$, $V_B^0$=(initial) volume of the bubbles at t=0, $V_B^t$ and $V_B^{t+\Delta t}$=volume of the bubbles at t and t+$\Delta t$, respectively. Equations of $V_B^t$ and $V_B^{t+\Delta t}$ are shown in FIG. 4. It is noted that $PBE^t$ is analogous to percent retained in each sieve measured during sieve analysis of aggregates. As a result, $PBE^t$ can be used to calculate the percent passing (PP) according to Equation 7, where $PP^t$ is percent passing at time t.

$$PBE^t = \frac{V_B^t - V_B^{t+\Delta t}}{V_B^0} \times 100 \quad (6)$$

$$PP^t = 100 - \sum_{i=0}^{t_i=t} PBE^{t_i} \quad (7)$$

Once the bubble size distribution is known, the number and total surface area of the bubbles can be computed according to Equations 8 and 9, where $N_B$=number of bubbles, $V_B^t$=total volume of the bubbles escaped at time t, $V_B^{single}$=volume of a single bubble=$4/3\pi R^3$, $S_B^t$=total surface area of the bubbles escaped at time t, $S_B^{single}$=surface area of a single bubble=$4\pi R^2$, R=average radius of bubbles escaped at time t. Combining Equations 5 and 6 and substituting the values of $V_B^{single}=4/3\pi R^3$, $S_B^{single}=4\pi R^2$ and R=D/2 provides the bubble surface area according to Equation 10, where $S_B^t$=surface area and $D^t$=average diameter of bubbles escaped from the foam at time t. Total bubble surface area of all the bubbles can be calculated by adding the $S_B^t$ values at different times according to Equation 11, where BSA=total surface area of all bubbles (in mm²) in the foam at time=0. A dimensionless parameter can be obtained by dividing the BSA by the surface area of the fluid in the container according to Equation 12, where SAI=surface area index (dimensionless), d=diameter of the container (FIG. 4) and $h^f$=final height of the binder after all the bubbles dissipate (FIG. 4). The SAI can be a useful dimensionless parameter for quantifying total surface generated by the foaming action and will influence the effectiveness of aggregate coating in WMA applications. It is also anticipated to relate to workability since small bubbles will lead to large SAI. Small bubbles typically do not collapse as fast as the large bubbles therefore the foam viscosity will stay low longer. This potentially leads to improved workability during placement and compaction.

$$N_B = \frac{V_B^t}{V_B^{single}} \quad (8)$$

$$S_B^t = N_B S_B^{single} \quad (9)$$

$$S_B^t = \frac{6 V_B^t}{D^t} \quad (10)$$

$$BSA = \sum_{i=0}^{\infty} S_B^{t_i} \quad (11)$$

$$SAI = \frac{BSA}{\pi d \left( h^f + \frac{d}{2} \right)} \quad (12)$$

Asphalt Foam Collapse Test (AFCT): As stated before, there were challenges in the methods presented in the literature for measuring foamed binder properties such as ER and half-life. During asphalt foam testing in base stabilization applications (for ER and half-life), measurements were facilitated by use of a fiducial marker (e.g., ruler) attached to the side of a container. This container is then filled with foamed binder and the height of the binder is recorded over time. However, this method is inaccurate due to the foamed binder opacity and results can be highly dependent on the operator. As mentioned previously, researchers have also utilized video image-based techniques. However, they were also based on visual observations of the foam height recorded within the video image. Automated image analysis techniques were not utilized. An automated, accurate and repeatable procedure is needed for measurement of reduction in height of foamed asphalt.

Sections below describe the AFCT, which is an automated test designed to measure the reduction in WMA foam height over time. With this continuous decay curve, calculations can then be made to determine all foam properties such as expansion ratio, foam index, half-life, bubble size distribution and surface area index.

Figure 5:
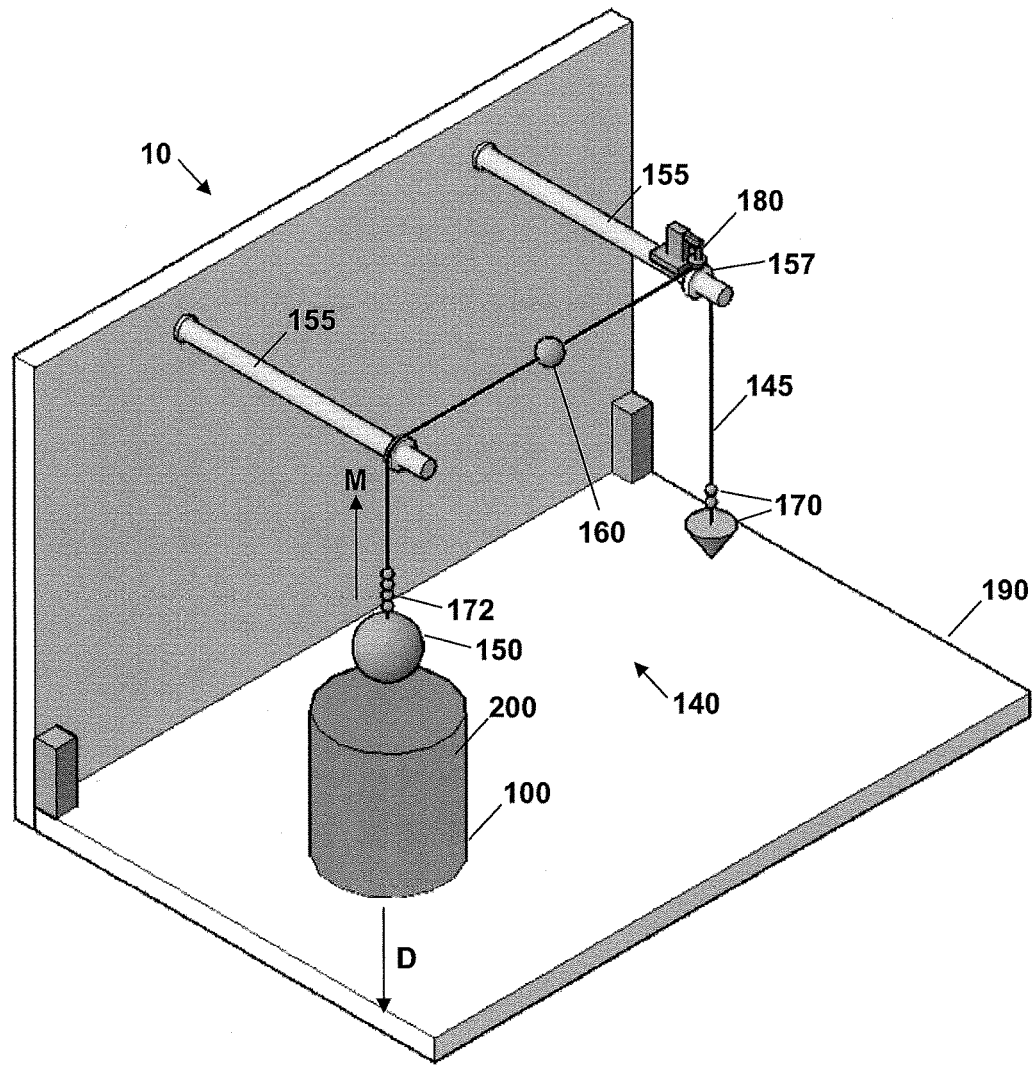
FIG. 5 illustrates a perspective view of an asphalt collapse foam testing apparatus according to the disclosure.
Figure 6:
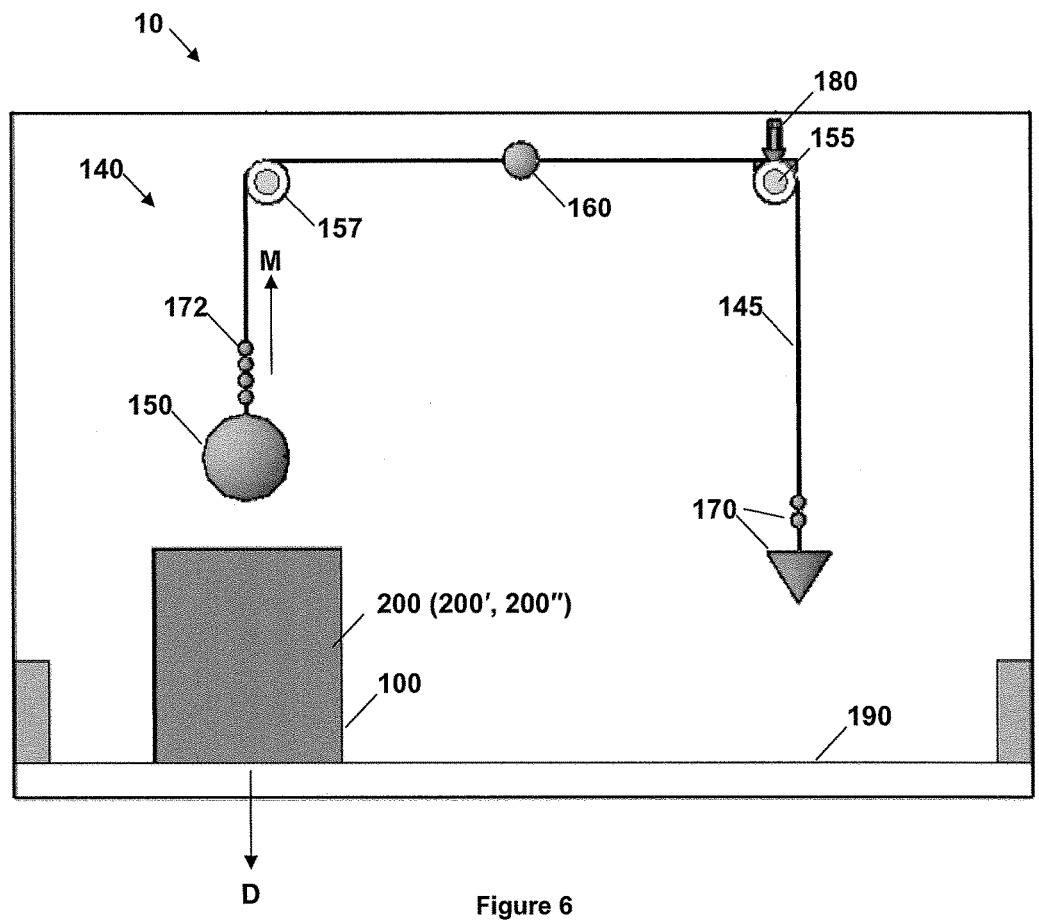
FIG. 6 illustrates a front view of an asphalt collapse foam testing apparatus according to the disclosure.
Figure 7:
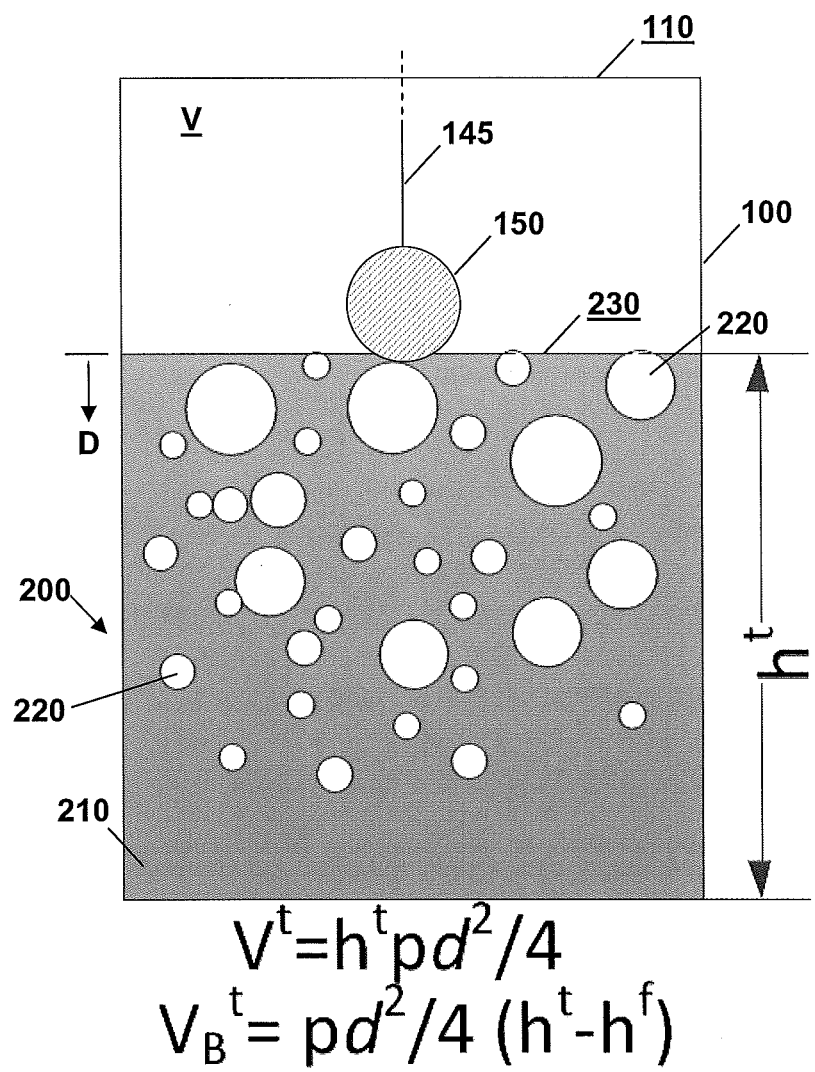
FIG. 7 is a schematic illustrating a foamed asphalt in a vessel at an arbitrary time t during a foam decay process, where $h^t$, $V^t$, and $V_B^t$ are the instantaneous foamed asphalt height, foamed asphalt volume, and bubble volume at time t in the vessel, respectively.

AFCT Setup: The AFCT apparatus 10 is illustrated in FIGS. 5 and 6 (camera and light source not shown). The setup includes a light source (light table) placed in between the two rods 155 shown in FIGS. 5 and 6, two precision bearings 157 bolted to the two individual rods 155, fishing line 145, weights 170, bobbers 150, 160, and a stopper 180. The precision bearings 157 provide frictionless rotation during the experiment. The rods 155 are mounted to an L-shaped wooden block 190 (or other support) as shown in the isometric view (FIG. 5). The stopper 180 is fixed on the rightmost rod 155 (as illustrated in FIGS. 5 and 6) and is used to release the fishing line 145 and start the experiment.

The first bobber 160, whose movement is captured using the camera, has a 2 cm diameter and is painted black. It is then fastened to the middle of the fishing line 145 using superglue. The second bobber 150 has a 4 cm diameter and is fully coated with asphalt binder to ensure that asphalt binder absorption on the bobber 150 during testing is negligible. Then, the weight of the binder coated bobber 150 is equalized to weights 170 attached to fishing line 145 on the stopper 180 side. Both the weights 170 and the bobber 150 were connected to the two ends of the fishing line 145 as shown in FIGS. 5 and 6. Finally, one gram weight 172 is attached to the bobber 150 side to ensure the free flow when the stopper 180 is released at the beginning of the experiment (e.g., one or more relatively small weights 172 can be used to ensure that the bobber 150 initially descends under gravity upon release until it contacts the upper surface of the foamed asphalt binder, where it remains buoyantly suspended on the top surface thereof during foam collapse).

During the AFCT test, a quart paint can 100 is filled with foamed binder 200 and placed under the bobber 150, and the bobber 150 is leveled to the surface of the foam 200. At that instant, the stopper 180 that fixes the fishing line 145 is released. As foam 200 collapses, the bobber 150 goes down with the surface 230 of the foamed binder 200, but it does not sink into the foamed binder 200. This is a crucial step during the test and can be ensured by balancing the two sides of the fishing line 145 well (e.g., using a combination of weights 170, 172 to ensure that the bobber 150 descends under gravity in an air medium and to further ensure that the buoyant force exerted by the foamed binder 200 during decay is sufficient to maintain the bobber 150 on the upper surface 230 of the binder 200 without sinking into the binder 200). Meanwhile, a camera captures the movement of the black painted bobber 160 while the foam 200 collapses. Since the bobbers 150 and 160 are on the same line, they move equal amounts and at equal rates.

AFCT Image Analysis: Image analysis techniques are used to calculate the movement of the bobber 160 with time, which corresponds to the change in the foam 200 height. Since the bobbers 150 and 160 are attached to the same line 145, they move the same distance. The bobber 160 moves horizontally while the bobber 150 moves vertically.

In order to record the video images, a smart phone camera was used. This allows the system to be easily transported to the field. The accuracy of the smart phone camera was validated against a high-speed industrial camera. The high-speed industrial camera captured 400 frames per second (fps), whereas the smart phone camera captured 30 fps. In order to check the frame rate, a timer was also placed at the top of the setup and included in the video images. Additionally, an 8× Optical Zoom Lens was connected to the smart phone to capture the foam collapse from approximately 2 m away. This facilitated the overall operation.

Once a video is captured, first, the frame rate was verified using a non-commercial video editing software (VIRTUALDUB). Then, images were extracted from the video file every 1 second and analyzed. The movement of the black painted bobber 160 versus time was computed using an algorithm developed in mathematical analysis software (MATLAB). In this algorithm, first, each image is converted to a binary (black/white) image through a thresholding operation such that only the bobber is black and the rest of the image (background) is white. It is noted that, since the fishing line 145 was relatively transparent, with the aid of the background lighting, it disappeared when the original image was converted to binary image. As a result, in each image, only a black circle (i.e., corresponding to the bobber 160) was visible. The center coordinate of the black circle was determined using a morphological labeling operation (Kutay et al. 2010, 2011). This procedure was repeated for all consecutive images. The change in the x-coordinate of the center of the bobber 160 in consecutive images corresponds to the change in the height of the bobber 150 and of the foam 200.

Water Content and Air Pressure: Selection of water content and air pressure can have a significant impact on the morphology of the bubbles. In order to investigate this, a PG 58-28 unmodified binder was foamed using a laboratory foamer (FIG. 1). The foaming temperature was 155° C. Each experiment was repeated three times. As shown in Table 2, the binder was foamed at two different water contents and under three different nozzle air pressures.

TABLE 2

Foam WMA binder parameters

| Binder Temp. (° C.) | Water Content (%) | Air Nozzle Pressure (psi) | Number of Samples |
| --- | --- | --- | --- |
| 155 | 1 | 10 | 3 |
| 155 | 1 | 15 | 3 |
| 155 | 1 | 20 | 3 |

TABLE 2-continued

Foam WMA binder parameters

| Binder Temp. (° C.) | Water Content (%) | Air Nozzle Pressure (psi) | Number of Samples |
| --- | --- | --- | --- |
| 155 | 4 | 10 | 3 |
| 155 | 4 | 15 | 3 |
| 155 | 4 | 20 | 3 |

Figure 8:
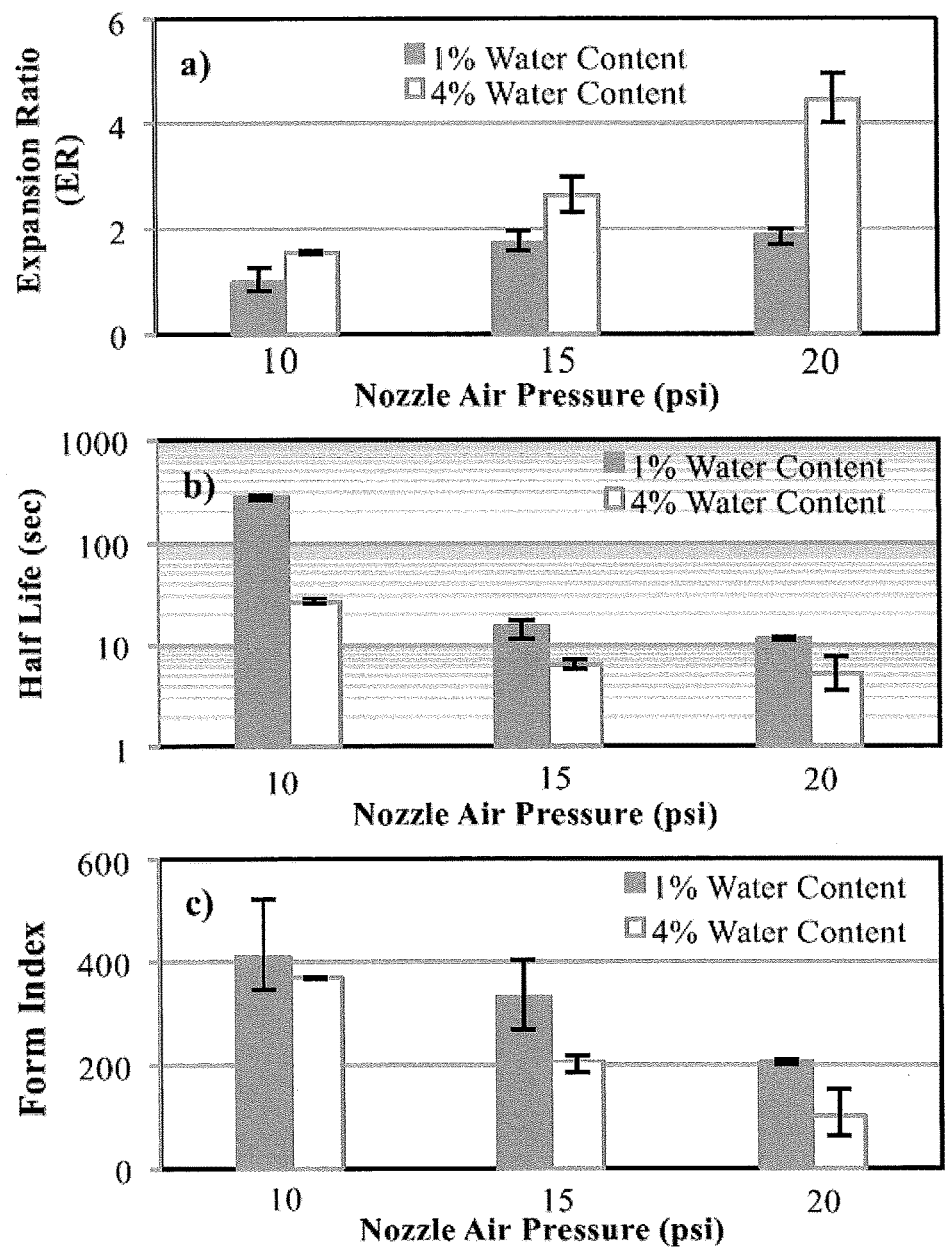
FIG. 8 includes graphs illustrating the variation of (a) Expansion Ratio, (b) Half Life, and (c) Foam Index with different water contents and air pressures.

The AFCT setup was used to measure the reduction in height of the foam with time. All tests were conducted on the same day to minimize the variability. FIG. 8a, FIG. 8b, and FIG. 8c show the ER, half-life and FI variations for the foamed binder at different water contents and air pressures, respectively. As shown in FIG. 8a, water content and air pressure have significant effect on the ER. ER increases with the increase of water content and air pressure and directly influences the total volume of the bubbles.

FIG. 8b shows that half-life decreases with increasing air pressure and water content. It should be recalled that, based on Stoke's law, large bubbles should rise to the surface faster and dissipate quicker. As a result, half-life is shorter. Combining the information in FIG. 8a and FIG. 8b, one can deduce that at large pressure and water content, larger bubbles are generated.

FIG. 8c shows the foam index (FI) (the area under ER versus time curve), which is measure of a combination of ER and half-life. The FI is an indirect indicator of overall surface area of the bubbles. If ER is large (i.e., more bubble volume) and half-life is large (i.e., small bubbles—more surface area for a given volume), FI will be also large, leading to large overall surface area. FIG. 8c indicates that overall surface area of the bubbles is large in low water content and low air pressure.

Figure 9:
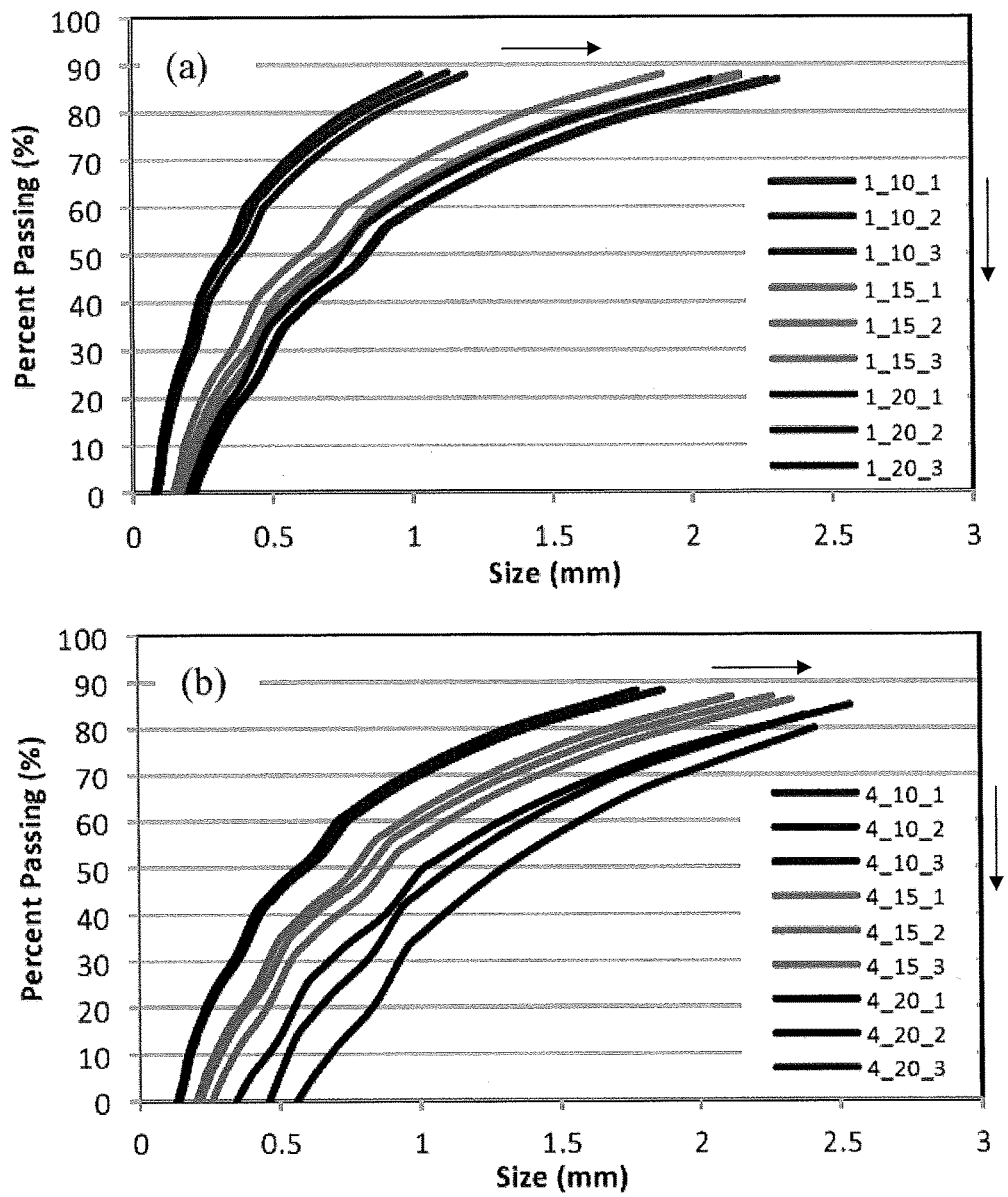
FIG. 9 includes graphs illustrating the bubble size distribution of the foamed binders at (a) 1% water and (b) 4% water contents.

FIG. 9a and FIG. 9b show the bubble size distribution of the foamed binder at two different water contents (1% and 4% of the binder). Equations 4 through 7 were used to generate these graphs. The legends of the graphs include the water content, air nozzle pressure and sample number. For example, 4_10_1 stands for 4% water content, 10 psi air nozzle pressure and 1 sample number (replicate). Viscosity of the unmodified binder was determined by following Standard Method of Test for Viscosity Determination of Asphalt Binder Using Rotational Viscometer (AASHTO T316). The viscosity of the binder was measured as 0.227 Pa·s at 155° C. It is clear that the increase in the air pressure makes the BSD coarser. In addition, as the water content increases, the gradations significantly become coarser.

Figure 10:
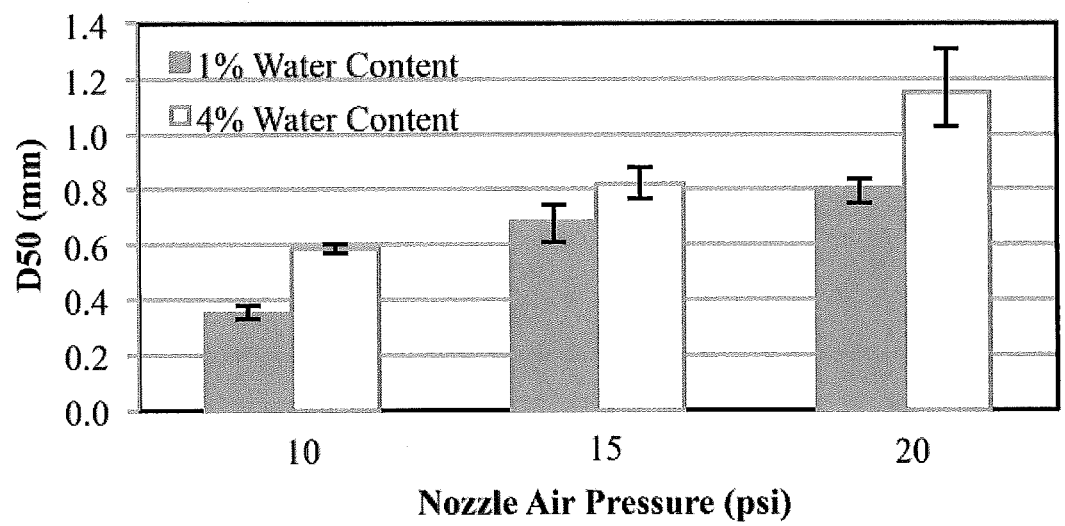
FIG. 10 includes a graph illustrating the average bubble size ($D_{50}$) of the steam bubbles in foamed binders.

The diameter of foamed binder at 50% of passing (D50) is plotted FIG. 10, where the effect of water content and air pressure on median bubble diameter is clearly visible. This supports the phenomenon observed in FIG. 8c, i.e., the increase in water content and air nozzle increases the size of the bubbles.

Figure 11:
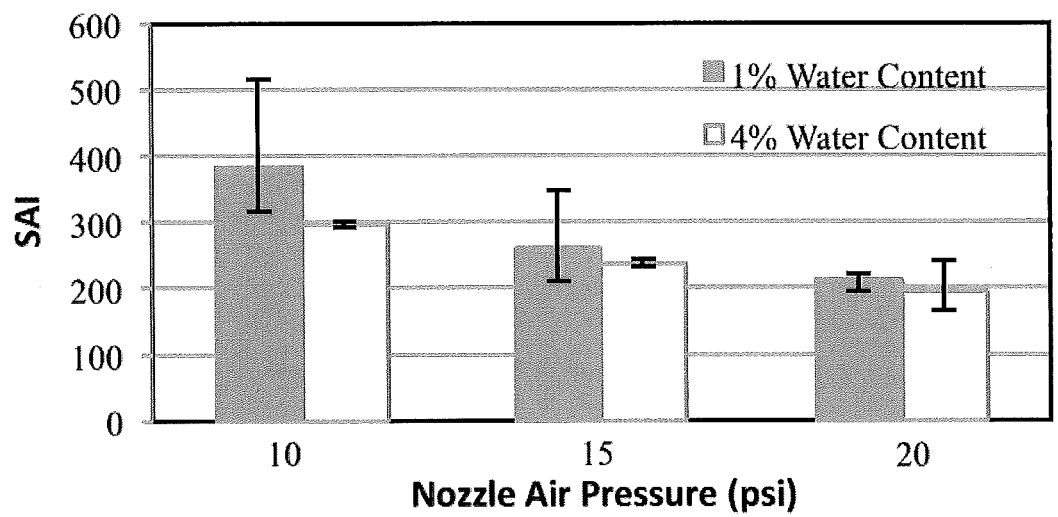
FIG. 11 includes a graph illustrating the surface area index (SAI) of the foamed binders foamed at different water contents and air pressures.

SAI (Equation 12) is a useful dimensionless parameter to evaluate the normalized total surface area. Small bubbles leads to larger SAI and do not collapse as fast as larger bubbles. Hence, the workability of WMA mixture improved due to low viscosity of foam binder for respectively longer time. However, it can affect the long term performance of the pavement if encapsulated small moisture bubbles exist after the pavement construction. Therefore, an optimum SAI range should be specified in foamed WMA applications. FIG. 11 shows the SAI values at different water contents and air pressures. As shown, largest overall surface area was observed in low water content/air pressure combination.

Figure 12:
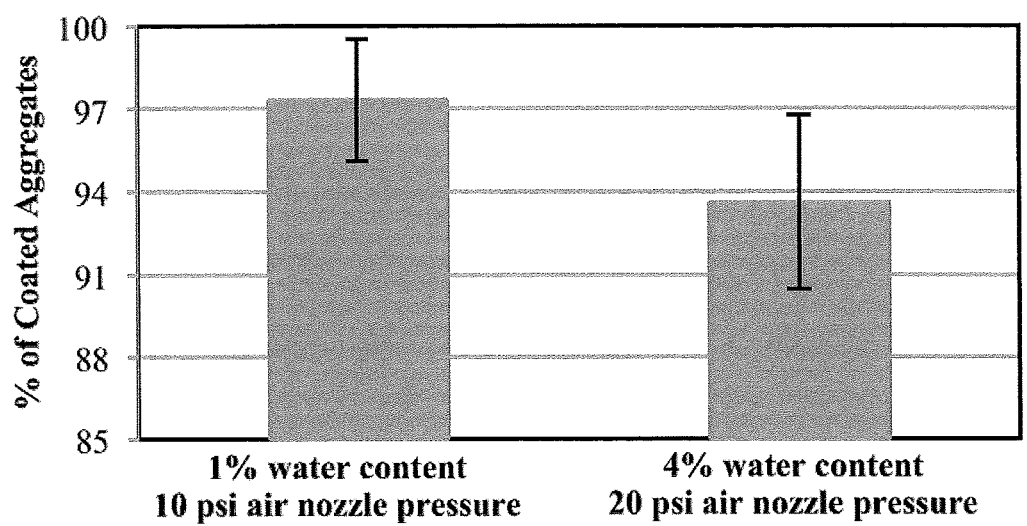
FIG. 12 includes a graph illustrating the effect of foamed binder on the percent of coated aggregates.

Influence on Aggregate Coating: The foamed binder has a significant effect on the coating of aggregates. Therefore, degree of coating should be determined by following the standard test method on Degree of Particle Coating of Asphalt Mixtures (AASHTO T195) before starting WMA mixture design. In NCHRP Reports 691 and 714, the coating criterion for the WMA mixtures was recommended to be 95%. In this study, two different water and air nozzle pressure combinations were selected to investigate the influence of the foamed binder properties on the coating. FIG. 12 shows that foamed binder with low water content and air pressure lead to better coating than high water content and air pressure. Comparing FIG. 11 and FIG. 12, one can see that large SAI resulted in better coating. This clearly supports the earlier hypothesis that if SAI is larger (i.e., small size bubbles), better coating is expected. It can be concluded that bubble size distribution and surface area index are significant 'quality' indicators for evaluating the ability of foamed binder to coat the aggregates.

Summary: This example illustrates a testing methodology called the Asphalt Foam Collapse Test (AFCT) for determining foamed binder properties such as expansion ratio, half-life and foam index. The AFCT is an automated, accurate and repeatable test method for measuring the height reduction of the foamed binder as it collapses. The AFCT is practical and affordable and can easily be transported to the field and measurements can be performed at the asphalt plant.

This example also illustrates a methodology to calculate the bubble size distribution and bubble surface area of the foamed binder from AFCT results. A dimensionless parameter called Surface Area Index (SAI), which was directly related to the mixture coating, was evaluated. The example illustrates the following: (1) The expansion ratio (ER) is an indicator of overall volume of bubbles, but it can be a misleading parameter for the size distribution of the bubbles that affects the coating and workability. (2) Water content and air pressure have significant effect on the ER, half-life (HL) and foam index (FI). ER increases with the increase of water content and air pressure, whereas HL and FI decreases with the increase of water content and air pressure. (3) The size distribution of the bubbles in foamed binder becomes coarser as the water content and air pressure increase. (4) SAI increases with decreasing water content and air pressure. Also, better mixture coating was observed at high SAI values.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

REFERENCES

1. AASHTO Standard Specifications for Transportation Materials and Methods of Sampling and Testing (Part 2—Tests), Twenty-Sixth Edition, American Association of State Highway and Transportation Officials, Washington, D.C., 2011.
2. ASTM Designation D1173-53 (Reapproved 1986), "Standard Test Method for Foaming Properties of Surface-Active Agents (a.k.a. Ross and Miles Test)", American Society for Testing and Materials: Philadelphia, Pa., 1988.
3. ASTM Designation D1881-86, "Standard Test Method for Foaming Tendencies of Engine Coolants in Glassware", American Society for Testing and Materials: Philadelphia, Pa., 1988.
4. ASTM Designation D3519-88, "Standard Test Method for Foam in Aqueous Media (Blender Test)", American Society for Testing and Materials: Philadelphia, Pa., 1988.
5. ASTM Designation D3601-88, "Standard Test Method for Foam in Aqueous Media (Bottle Test)", American Society for Testing and Materials: Philadelphia, Pa., 1988.
6. ASTM Designation D892-74 (Reapproved 1984), "Standard Test Method for Foaming Characteristics of Lubricating Oils", American Society for Testing and Materials: Philadelphia, Pa., 1988.
7. Bennert, T. "Evaluation of Warm Asphalt Technology—Feasibility Study" NJDOT Project 2008-1, Center for Advanced Infrastructure and Transportation, Rutgers University, 2008.
8. Brennen, M. T., Altschaeffl, A. G. and Wood, L. E., "Laboratory Investigation of the use of Foamed Asphalt for Recycled Bituminous Pavements", Transportation Research Record: Journal of the Transportation Research Board, 911, 80-87, 1983.
9. Bonaquist, R. "Mix Design Practices for Warm Mix Asphalt", NCHRP Report 691, Transportation Research Board of the National Academies. Washington, D.C., 2011.
10. D'Angelo, J., Harm, E., Bartozsek, J., Baumgardner, G., Corrigan, M., Cowsert, J., Harman, T., Jamshidi, M., Jones, W., Newcomb, D., Prowell, B., Sines, R. and Yeaton B., "Warm Mix Asphalt: European Practice", FHWA report no: FHWA-PL-08-007, 2008.
11. Das, B. M. "Principles of Geotechnical Engineering", Cengage Learning, Stamford, Conn., $7^{th}$ edition, 2009.
12. Haffmans, B. V., NIBEM Foam Stability Tester product brochure, 2004.
13. Hassan, M. M. "Life-Cycle Assessment of Warm-Mix Asphalt: an Environmental and Economic Perspective", Transportation Research Board (TRB), 88th Annual Meeting Compendium of Papers DVD, Washington, D.C., 2009.
14. He, G. and Wong W., "Decay properties of the foamed bitumens", Construction and Building Materials, 20, 866-877, 2006.

15. Jenkins, K. J., "Mix Design Considerations for Cold and Half-warm Bituminous Mixes with emphasis on Foamed Bitumen", PhD Dissertation, University of Stellenbosch, South Africa, 2000.
16. Kim, Y., Lee H., and Heitzman, M. "Validation of New Mix Design Procedure for Cold In-place Recycling with Foamed Asphalt for Iowa Department of Transportation", Transportation Research Board (TRB) Annual Meeting CD-ROM, 2006.
17. Kutay, M. E. and Ozturk, H. "Investigation of Moisture Dissipation in Foam-based Warm Mix Asphalt Using Synchrotron-Based X-Ray Microtomography", ASCE Journal of Materials in Civil Engineering, Vol. 24, No 6, pp. 674-683, 2012.
18. Kutay, M. E., Arambula, E., Gibson, N. H. and Youtcheff, J. "Three-Dimensional Image Processing Methods to Identify and Characterize Aggregates in Compacted Asphalt Mixtures", International Journal of Pavement Engineering, Vol. 11, Issue 6, pp. 511-528. 2010.
19. Kutay, M. E., Ozturk, H., Abbas, A. and Hu, C "Comparison of 2D and 3D Image-Based Aggregate Morphological Indices", International Journal of Pavement Engineering, Vol. 12, Issue 4, pp. 421-431. 2011.
20. Kristjánsdóttir, O., Muench, S. T., Michael, L. and Burke, G., "Assessing the potential for Warm Mix Technology Adoption", Transportation Research Record: Journal of the Transportation Research Board, No. 2040, Washington D.C., 2007.
21. Lamb, H. "Hydrodynamics", Cambridge, England: Cambridge University Press, pp. 597. 1932.
22. Leek, C. and Jameson G., "Review of Foamed Bitumen Stabilisation Mix Design Methods", Austroads Technical Report, Austroads Publication No. AP-T178/11, 2011.
23. Maine DOT, "Maine's Experience Utilizing Full Depth Reclamation with Foamed Asphalt", presentation at NESMEA 2004, Portsmouth, N.H., 2004.
24. Mallick, R. B., Bergendahl, J. and Pakula, M. "A Laboratory Study on CO2 Emission Reductions through the Use of Warm Mix Asphalt", Transportation Research Board 2009 Annual Meeting, Washington, D.C. 2009.
25. Muthen, K. M., "Foamed Asphalt Mixes: Mix Design Procedure", CSIR TRANSPORTEK Report No: CR-98/077, South Africa, 1998.
26. Nadeau, G., "Warm Mix and the 'Every Day Counts' Initiative", Asphalt Pavement, National Asphalt Pavement Association (NAPA), pp. 16-21., 2012
27. Namutebi, M. "Some Aspects of Foamed Bitumen Technology", Licentiate Thesis, Division of Highway and Railway Engineering, Department of Transport Science School of Architecture and the Built Environment, Royal Institute of Technology SE100 44 Stockholm, 2011.
28. NCHRP Report 714, "Special Mixture Design Considerations and Methods for Warm Mix Asphalt: A supplement to NCHRP Report 673: A Manual for Design of Hot Mix Asphalt with Commentary", Transportation Research Board of the National Academies. Washington, D.C., 2012.
29. Neu, G. E., "Techniques of Foam Measurement" Journal of Society of Cosmetic Chemists, V.11, No. 7, Pp. 390-414, 1960.
30. Prowell, B. D. "Warm Mix Asphalt: The international technology scanning program summary report", U.S. Department of Transportation, Federal Highway Administration American Association of State Highway and Transportation Officials, National Cooperative Highway Research Program, 2007.
31. Prowell, B., D., Hurley, G. and Frank, B., Warm Mix Asphalt: Best Practices, National Asphalt Pavement Association (NAPA) Quality Improvement Publication 125, $3^{rd}$ Ed., 65p. 2012.
32. Saleh, M., "Characterization of Foam Bitumen Quality and the Mechanical Properties of Foam Stabilized Mixes", 10th International Conference on Asphalt Pavements (ICAP 2006), Quebec City, Canada, 2006.
33. Schramm, L. L., "Emulsions, Foams, and Suspensions: Fundamentals and Applications", WILEY-VCH Verlag GmbH & Co. KGaA, Weinheim, 2005.
34. Sebba, F., "Foams and Biliquid Foams—Aphrons", Wiley: NewYork, 1987.

What is claimed is:

1. A method for forming an asphalt concrete composition, the method comprising:
    (a) introducing bubbles into an asphalt medium to form a foamed asphalt comprising the asphalt medium and a plurality of the bubbles dispersed throughout the asphalt medium;
    (b) allowing the foamed asphalt to decay and measuring the amount of the foamed asphalt as a function of time during decay to provide an amount time series for the decaying foamed asphalt;
    (c) determining from the amount time series at least one foam quality parameter selected from the group consisting of bubble size distribution parameters, bubble surface area parameters, and combinations thereof;
    (d) comparing the foam quality parameter determined from the amount time series with at least one user-selected foam quality criterion selected from an acceptable minimum value, an acceptable maximum value, and an acceptable range of values for the foam quality parameter; and
    (e) after (d), mixing aggregate with the foamed asphalt to provide the asphalt concrete composition.

2. The method of claim 1, wherein at least one foam quality parameter is a bubble size distribution parameter.

3. The method of claim 2, wherein:
    (i) the bubble size distribution parameter is an average bubble size of the distribution of bubbles prior to measuring the amount of the foamed asphalt as a function of time, and
    (ii) the corresponding quality criterion is selected from the group consisting of an acceptable minimum value for the average bubble size, an acceptable maximum value for the average bubble size, and an acceptable range for the average bubble size.

4. The method of claim 1, wherein at least one foam quality parameter is a bubble surface area parameter.

5. The method of claim 4, wherein the bubble surface area parameter is a normalized total surface area of all bubbles present in the foamed asphalt prior to measuring the amount of the foamed asphalt as a function of time.

6. A method for forming an asphalt concrete composition, the method comprising:
    (a) introducing bubbles into an asphalt medium to form a foamed asphalt comprising the asphalt medium and a plurality of the bubbles dispersed throughout the asphalt medium;
    (b) allowing the foamed asphalt to decay and measuring the height of the foamed asphalt along a measurement axis and as a function of time during decay to provide a height time series for the decaying foamed asphalt, wherein the measurement axis is substantially parallel to a decay direction defined by the decaying foamed asphalt;

(c) determining from the height time series at least one foam quality parameter;

(d) comparing the foam quality parameter determined from the height time series with at least one foam quality set point criterion selected from an acceptable minimum value, an acceptable maximum value, and an acceptable range of values for the foam quality parameter; and (e) after (d), mixing aggregate with the foamed asphalt to provide the asphalt concrete composition.

7. The method of claim 6, wherein the foam quality parameter is selected from the group consisting of bubble size distribution parameters, bubble surface area parameters, integral decay properties, characteristic decay times, and combinations thereof.

8. The method of claim 6, further comprising: adding a buoyant marker to an external surface of the foamed asphalt, wherein measuring the height of the foamed asphalt comprises measuring the height of the buoyant marker.

9. The method of claim 8, wherein the buoyant marker is sufficiently sized to reduce erratic movement of the buoyant marker resulting from bubbles escaping from the foamed binder during decay.

10. A method for forming an asphalt concrete composition, the method comprising:
(a) introducing bubbles into a first asphalt medium at a first set of foam generation conditions to form a first foamed asphalt comprising the first asphalt medium and a plurality of the bubbles dispersed throughout the first asphalt medium;
(b) determining foamed asphalt quality according for the first foamed asphalt by (i) allowing the first foamed asphalt to decay and measuring the amount of the first foamed asphalt as a function of time during decay to provide a first amount time series for the decaying first foamed asphalt, and (ii) determining from the first amount time series at least one first foam quality parameter selected from the group consisting of bubble size distribution parameters, bubble surface area parameters, and combinations thereof;
(c) introducing bubbles into a second asphalt medium at a second set of foam generation conditions different from the first set of foam generation conditions to form a second foamed asphalt comprising the second asphalt medium and a plurality of the bubbles dispersed throughout the second asphalt medium;
(d) determining foamed asphalt quality according for the second foamed asphalt by (i) allowing the second foamed asphalt to decay and measuring the amount of the second foamed asphalt as a function of time during decay to provide a second amount time series for the decaying first foamed asphalt, and (ii) determining from the second amount time series at least one second foam quality parameter selected from the group consisting of bubble size distribution parameters, bubble surface area parameters, and combinations thereof; and
(e) after (d), mixing aggregate with at least one of the first foamed asphalt and the second foamed asphalt to provide the asphalt concrete composition.

11. The method of claim 10, comprising performing parts (a)-(d) as an automated process in a feedback control loop.

12. The method of claim 1, wherein the aggregate is selected from the group consisting of stone, gravel, sand, and combinations thereof.

13. The method of claim 1, wherein:
(i) the asphalt medium is present in an amount ranging from 2 wt. % to 10 wt. % relative to the asphalt concrete composition; and
(ii) the aggregate is present in an amount ranging from 90 wt. % to 98 wt. % relative to the asphalt concrete composition.

14. A method for forming multiple asphalt concrete compositions, the method comprising:
(a) performing the method of claim 1 to form at least two asphalt concrete compositions, wherein:
(i) the aggregate has a different characteristic size in each composition; and
(ii) the foamed asphalt has a selected different foam quality corresponding to the aggregate characteristic size in each composition.

* * * * *